(12) United States Patent
Kleinberg et al.

(10) Patent No.: US 9,408,887 B2
(45) Date of Patent: Aug. 9, 2016

(54) INTERMITTENT DOSING REGIMEN FOR TREATING BREAST CANCER

(71) Applicants: David L. Kleinberg, New York, NY (US); Mary Helen Barcellos-Hoff, New York, NY (US)

(72) Inventors: David L. Kleinberg, New York, NY (US); Mary Helen Barcellos-Hoff, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/487,197

(22) Filed: Sep. 16, 2014

(65) Prior Publication Data

US 2015/0099700 A1    Apr. 9, 2015

Related U.S. Application Data

(62) Division of application No. 13/564,873, filed on Aug. 2, 2012, now Pat. No. 8,835,123.

(60) Provisional application No. 61/574,414, filed on Aug. 2, 2011.

(51) Int. Cl.
*A61K 38/12* (2006.01)
*A61K 38/31* (2006.01)
*G01N 33/574* (2006.01)

(52) U.S. Cl.
CPC ............ *A61K 38/12* (2013.01); *A61K 38/31* (2013.01); *G01N 33/57415* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 6,946,256 B1 | 9/2005 | McKeon et al. ............... 435/7.1 |
| 7,473,761 B2 | 1/2009 | Albert et al. |
| 2009/0325863 A1 | 12/2009 | Kleinberg et al. |

OTHER PUBLICATIONS

DiLeo et al. (Breast Cancer Res Treat. Jun. 1995;34(3):237-244).*
Kahan et al., Int J Cancer. Aug. 12, 1999;82(4):592-598.*
Ruan, W et al (2006) Mol Endocrinology 20(2):426-436.*
Wright et al., "BRCA1 breast tumors contain distinct CD44+/CD24− and CD133+ cells with cancer stem cell characteristics", Breast Cancer Research, 2008, 10, 1-16.
Burga et al., "Altered proliferation and differentiation properties of primary mammary epithelial cells from BRCA1 mutation carriers", Cancer Research, 2009, 69, 1273-1278.
Lim et al., "Aberrant luminal progenitors as the candidate target population for basal tumor development in BRCA1 mutation carriers", Nature Medicine, 2009, 15, 907-913.
Molyneux et al., "BRCA1 basal-like breast cancers originate from luminal epithelial progenitors and not from basal stem cells", Cell Stem Cell, 2010, 7, 403-417.
Lamberts et al., "The role of somatostatin and its analogs in the diagnosis and treatment of tumors", Endocrin Rev, 1991, 12, 450-481.

Patel et al., "The somatostatin receptor family", Life Sciences, 1995, 57, 1249-1265.
Patel et al., "Molecular biology of somatostatin receptor subtypes", Metabolism, 1996, 45, 31-38.
Reisine et al., "Molecular biology of somatostatin receptors", Endocrin Rev, 1995, 16, 427-442.
Buscail et al., "Inhibition of cell proliferation by the somatostatin analogue RC-160 is mediated by somatostatin receptor subtypes SSTR2 and SSTR5 through different mechanisms", Proc Natl Acad Sci, 1995, 92, 1580-1584.
Bell et al., "Molecular biology of somatostatin receptors", Trends Neuroscience, 1993, 16, 34-38.
Ruan et al., "SOM230 inhibits insulin-like growth factor-I action in mammary gland development by pituitary independent mechanism: Mediated through somatostatin subtype receptor 3?", Molecular Endocrinology, 2006, 20, 426-436.
London et al., "A prospective study of benign breast disease and the risk of breast cancer", JAMA, 1992, 267, 941-944.
Palli et al., "Benign breast disease and breast cancer: A case-control study in a cohort in Italy", Int J Cancer, 1991, 47, 703-706.
Dupont et al., "Risk factors for breast cancer in women with proliferative breast disease", N Engl J Med, 1985, 312, 146-151.
Dupont et al., "Breast cancer risk associated with proliferative breast disease and atypical hyperplasia", Cancer, 1993, 71, 1258-1265.
Hartmann et al., "Benign breast disease and the risk of breast cancer", N Engl J Med, 2005, 353, 229-237.
Morrison et al., "Asymmetric and symmetric stem-cell divisions in development and cancer", Nature, 2006, 441, 1068-1074.
Fleseriu et al., "Medical management of Cushing's Disease: What is the future?", Pituitary, 2012, 15, 330-341.
Colao et al., "A 12-month phase 3 study of pasireotide in Cushing's Disease", N Eng J Med, 2012, 366, 914-924.
Ruan et al., "Progesterone stimulates mammary gland ductal morphogenesis by synergizing with and enhancing insulin-like growth factor-I action", Endocrinology, 2005, 146, 1170-1178.
Boccardo et al., "Management of breast cancer: Is there a role for somatostatin and its analogs?", Chemotherapy, 2001, 47, 62-77.
Fedele et al., SOM230, a new somatostatin analogue, is highly effective in the therapy of growth hormone/prolactin-secreting pituitary adenomas, Clin Cancer Res, 2007, 13, 2738-2744.

(Continued)

*Primary Examiner* — Daniel C Gamett
(74) *Attorney, Agent, or Firm* — Klauber & Jackson LLC

(57) ABSTRACT

Diagnostic and therapeutic methods pertaining to diseases and disorders of the breast, uterus and ovary are encompassed herein. More particularly, diagnostic methods for early detection of progenitor cells of breast, uterine, and ovarian cancers are described herein. The identification of markers for these cancer predisposing progenitor cells, which co-express the progesterone receptor (PR) and p63, provides tools and methods of use thereof that facilitate early detection of increased frequency of PR/p63 double positive (PR/p63+) progenitor cells in asymptomatic patients and thus, early detection of increased cancer risk in such patients and assessment, diagnostic stratification, and evaluation of therapeutic intervention in symptomatic patients. Therapeutic methods are also encompassed herein, which include detection of PR/p63+ progenitor cells in a patient, wherein detection of increased frequency of PR/p63+ progenitor cells provides information on which basis a determination of therapeutic regimen or an assessment of an ongoing therapeutic regimen can be made.

9 Claims, 5 Drawing Sheets

(56) References Cited

OTHER PUBLICATIONS

Dewar et al., "Best practices in diagnostic immunohistochemistry", Arch Pathol Lab Med, 2011 135, 422-429.

Ribeiro-Silva et al., "The relationship between p63 and p53 expression in nomial and neoplastic breast tissue", Arch Pathol Lab Med, 2003, 127, 336-340.

Liu et al., "BRCA1 regulates human mammary stemlprogenitor cell fate", Proc Natl Acad Sci, 2008, 105, 1680-1685.

Lim et al., "Transcriptome analyses of mouse and human mammary cell subpopulations reveal multiple conserved genes and pathways", Breast Cancer Research, 2010, 12, 1-14.

Fernandez-Gonzalez et al., "Mapping mammary gland architecture using multi-scale in situ analysis", Integr Biol, 2009, 1, 80-89.

Westfall et al., "p63: molecular complexity in development and cancer", Carcinogenesis, 2004, 25, 857-864.

Hill et al., "Myoepithelial cell staining patterns of papillary breast lesions", Am J Clin Pathol, 2005, 123, 36-44.

Batistatou et al., "The usefulness of p63 as a marker of breast myoepithelial cells", In vivo, 2003, 17, 573-576.

Sukerkar et al., "A steroid-conjugated magnetic resonance probe enhances contrast in progesterone receptor expressing organs and tumors in vivo", Mol Pharm, 2011, 8, 1390-1400.

Stefanou et al., "p63 expression in benign and malignant breast lesions", Histol Histopathol, 2004, 19, 465-471.

Werling et a., "Immunohistochemical distinction of invasive from noninvasive breast lesions", Am J Surg Pathol, 2003, 27, 82-90.

Reis-Filho et al., "Taking advantage of basic research: p63 is a reliable myoepithelial and stem cell marker", Advances in Anatomic Pathology, 2002, 9, 280-289.

Saad et al., "Fine-needle aspiration biopsy of breast adenomyoepithelioma: A potential false positive pitfall and presence of intranuclear cytoplasmic inclusions", Diagnostic Cytopathology, 2012, 40, 1005-1009.

Barbareschi et al., "p63, a p53 homologue, is a selective nuclear marker of myoepithelial cells of the human breast", Am J Surg Pathol, 2001, 25, 1054-1060.

Shukla et al., "IGF signaling pathway as a selective target of familial breast cancer therapy", Current Molecular Medicine, 2008, 8, 727-740.

Hudelist et al., "Intratumoral IGF-1 protein expression is selectively upregulated in breast cancer patients with BRCA1/2 mutations", Endocrine-Related Cancer, 2007, 14, 1053-1062.

Ng et al., "Altered serum levels of insulin-like growth-factor binding proteins in breast cancer patients", Annals of Surgical Oncology, 1998, 5, 194-201.

* cited by examiner

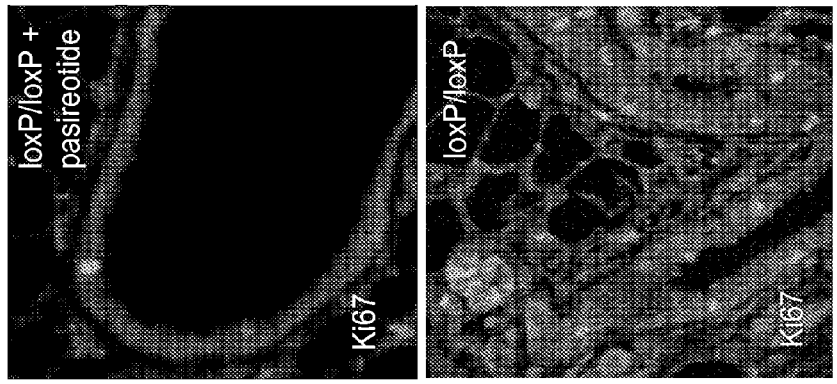
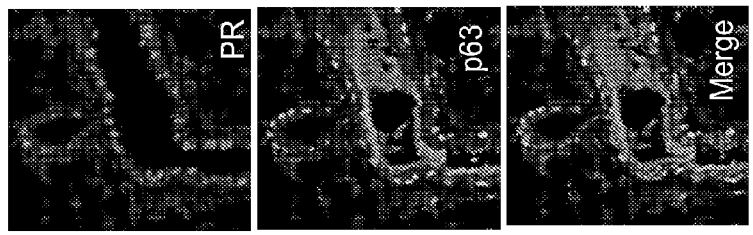
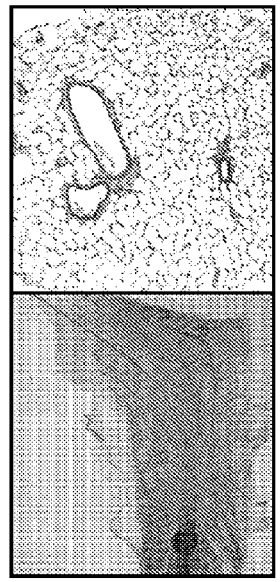
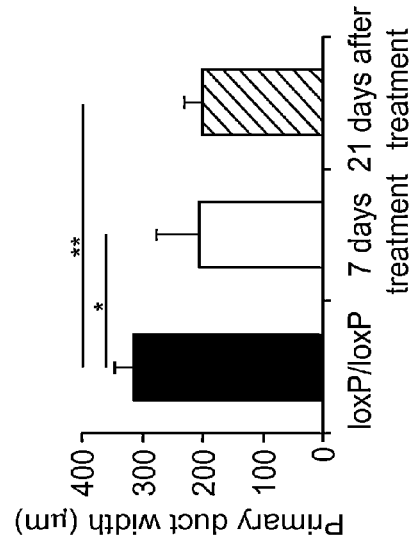
FIG. 3A
FIG. 3B
FIG. 3C
FIG. 3D
The loxP/loxP phenotype does not revert after treatment conclusion

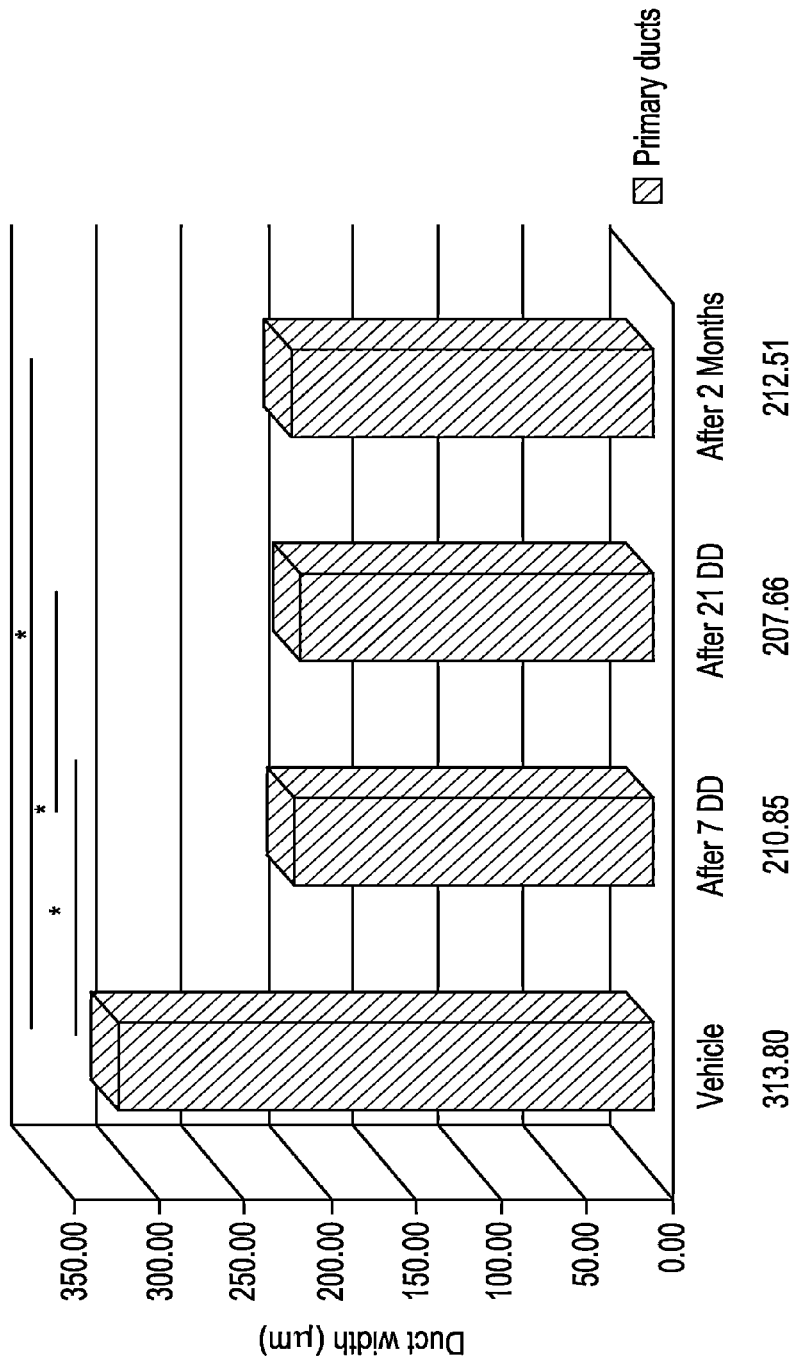

INTERMITTENT DOSING REGIMEN FOR TREATING BREAST CANCER

CROSS REFERENCE TO RELATED APPLICATIONS

The present application is a Divisional Application of U.S. Application Ser. No. 13/564,873, now U.S. Pat. No. 8,835,123, issued Sep. 16, 2014, which in turn claims priority under 35 USC §119(e) from U.S. Provisional Application Ser. No. 61/574,414, filed Aug. 2, 2011, each of which applications is herein specifically incorporated by reference in its entirety.

GOVERNMENTAL SUPPORT

The research leading to the present invention was supported, at least in part, by a grant from the Office of Biological and Environmental Research DE-FG01-08ER64654. Accordingly, the Government has certain rights in the invention.

FIELD OF THE INVENTION

The present invention relates generally to diagnostic and therapeutic methods pertaining to diseases and disorders of the breast, uterus and ovary. More particularly, the present invention relates to diagnostic methods for early detection of progenitor cells of breast, uterine, and ovarian cancers. The identification of markers for these progenitor cells that can predispose to cancer, which are described for the first time herein and co-express the progesterone receptor (PR) and p63, provides tools and methods of use thereof that facilitate early detection of increased frequency of PR/p63 double positive (PR/p63+) progenitor cells in asymptomatic patients and assessment, diagnostic stratification, and evaluation of therapeutic intervention in symptomatic patients. Therapeutic methods are also encompassed herein, which include detection of PR/p63+ progenitor cells in a patient, wherein detection of increased frequency of PR/p63+ progenitor cells provides information on which basis a determination of therapeutic regimen can be made.

In a further aspect, the invention relates to the use and application of compounds or agents that inhibit IGF-I receptor engagement and signaling for the treatment of conditions and diseases of the breast, uterus, and ovary wherein increased frequency of PR/p63+ progenitor cells is detected. In a particular aspect, the invention relates to the use and application of compounds or agents, including somatostatin analogs, with effect on, affinity for, or specificity to SSTR3 and/or SSTR5 somatostatin receptors for the treatment of conditions and diseases of the breast, uterus, and ovary wherein increased frequency of PR/p63+ progenitor cells is detected. The invention further relates to the use and application of compounds or agents, including somatostatin analogs, with effect on, affinity for, or specificity to SSTR3 and/or SSTR5 somatostatin receptors for the treatment of conditions and diseases of the breast, uterus, and ovary wherein increased frequency of PR/p63+ progenitor cells is detected and/or prevention or reduction of risk for BRCA1 associated breast cancer wherein increased frequency of PR/p63+ progenitor cells is detected. The invention also relates to use of somatostatin analog SOM230 in treatment of conditions and diseases of the breast, uterus, and ovary wherein increased frequency of PR/p63+ progenitor cells is detected and more particularly, to use of somatostatin analog SOM230 in treatment of BRCA1 associated conditions and diseases of the breast, uterus, and ovary wherein increased frequency of PR/p63+ progenitor cells is detected and/or prevention of BRCA1 associated breast cancer wherein increased frequency of PR/p63+ progenitor cells is detected in asymptomatic patients.

BACKGROUND OF THE INVENTION

Breast cancer arises in the epithelium of the organ. The epithelium consists of several cell types, each of which has a particular propensity to 'transform' into cancer. It is thought that the cell of origin confers upon the resulting tumor a particular phenotype, with the most aggressive tumors being derived from relatively undifferentiated cells whose replicative capacity is large. These include those designated as stem cells, capable of giving rise to the entire epithelium, and progenitor cells, capable of giving rise to progeny whose differentiation is restricted. The hierarchical distribution of these lineages poses that stem cells have the most replicative and regenerative capacity, while progenitors have less and differentiated cells have the least. Thus, the composition of the breast epithelium, in terms of distribution and frequency of specific cell types, can affect the risk of developing cancer and will also affect the type of cancer (Visvader (2011) Nature 469(7330): 314-322).

A case in point is the breast of women who carry germline mutations in BRCA1 and have a substantially greater risk of developing cancer of the breast, as well as the ovary and uterus. Breast cancer is heterogeneous. At least five distinct breast cancers subtypes have been identified based on any one of morphology, marker frequency or gene expression or a combination thereof. While breast cancer is most prevalent in women after the age of 60, BRCA1 mutation carriers have a much greater risk of developing an aggressive type of breast cancer even before the age of 40. This type of cancer is frequently designated triple-negative because it lacks expression of estrogen receptor (ER) and PR, and does not amplify HER2. The absence of markers suggests that it originates from undifferentiated cells. This conjecture is supported by recent studies showing that BRCA1 mutations cause an expansion of progenitor cells in breast (Liu, et al. 2008. Proc Natl Acad Sci USA 105(5): 1680-1685; Proia, et al. 2011. Cell stem cell 8(2): 149-163).

Breast cancer is the most common cancer in women and the second leading cause of cancer-related mortality in women. About 10% of breast cancer cases cluster in families. Mutations in the breast cancer susceptibility (BRCA) genes are correlated with a high percentage of these familial cases. Indeed, BRCA1 mutations account for the most common form of genetically inherited breast cancer. Germline mutations of BRCA1 have been detected in approximately 90% of familial breast and ovarian cancers and approximately 50% of familial breast cancer alone (Hill et al. 1997 *Br. J. Surg.* 84, 1334-1339; Casey. 1997. *Curr. Opin. Oncol.* 9, 88-93. Women that inherit germ cell mutations of BRCA1 are at up to 80% risk of developing breast cancer and 50% risk of developing ovarian cancer. BRCA mutation carriers are also typically diagnosed with invasive breast cancer about ten years earlier than patients presenting with sporadic breast cancer. BRCA1 associated cancers, moreover, exhibit distinct histopathology, immunohistochemistry, cytogenetics, and gene expression profiles that differ from those of either non-familial breast cancer cases or BRCA2-related breast cancer.

Even though most BRCA1 mutations lead to estrogen receptor negative breast cancer, treatment with estrogen increases cancer risk in BRCA1 mutation carriers. Also there is a high degree of hyperplastic lesions in women with mutations in the BRCA1 gene when their breast tissue is examined following prophylactic mastectomies performed to avoid development of breast cancer (Hoogerbrugge N J Clin Oncology 2003, 41-45).

Women with certain hyperplastic lesions of the breast are at high risk for breast cancer. There is clinical evidence that treatment with tamoxifen can prevent the development of cancer by about 50%. Tamoxifen treatment is problematic in that it has many side effects and makes women almost completely estrogen deficient as if they were menopausal. Serious side effects include uterine cancer, pulmonary embolism, and strokes. Although well tolerated by some patients, many patients experience one or more unpleasant side effects and some experience life threatening complications as a result of tamoxifen treatment. Indeed, some patients consider the side effects of tamoxifen treatment to be unacceptable.

With respect to BRCA1 mutation carriers, however, even tamoxifen, which is effective in preventing most sporadic breast cancers, is not known to be an effective preventive measure (King M C et al, JAMA 2001 2251-2256). Due to their high risk for developing breast cancer and limited preventive options, many BRCA1 mutation carriers feel compelled to turn to prophylactic bilateral mastectomy as the only proven method for preventing development of breast cancer (Meijers-Heijboer, H N Eng J Med 2001 159-164). Bilateral oophorectomy is also an available option, but is known to be less protective (Rebbeck, T R et al J Natl Cancer Inst 1999, 1475-1479).

Antiestrogens or aromatase inhibitors have also been employed as a means of preventing breast cancer in women with preneoplastic breast lesions such as atypical hyperplasia. While effective in women with atypical hyperplasia, these approaches may cause serious side effects and symptoms of menopause which can be unacceptable, and also a high incidence of osteoporosis. These techniques are also utilized to prevent recurrence of breast cancer in women with ductal carcinoma in situ. Ruan et al. have proposed that inhibition of insulin-like growth factor 1 (IGF-I or IGF-1) activity might be able to substitute for estrogen inhibitors because IGF-I is essential for estrogen and progesterone action in the mammary gland (Ruan W et al (2005) Endocrinology 146(3): 1170-1178).

Somatostatin and somatostatin-related peptides are a family of peptides that have broad spectrum biological actions and exert suppressive effects on a large variety of cells, functioning as endogenous growth inhibitors. Naturally-occurring peptides have a short half life because they are rapidly inactivated by endogenous peptidases and therefore efforts have been made to develop more stable peptides. The three most extensively tested analogs are SMS 201-995 (octreotide), BIM 23014 (lanreotide) and RC-160 (vapreotide) (Lamberts S W J et al (1991) Endocrin Rev 12:450-482). Somatostatins bind somatostatin receptor(s), with subtypes SSTR-1 to SSTR-5 identified, cloned, and functionally characterized (Patel Y C et al (1995) Life Sci 57:1249-1265; Patel Y C et al (1996) Metabolism 45 (suppl 1):31-38; Reisine T and Bell G I (1995) Endocrin Rev 16:427-442; Buscail L et al (1995) PNAS USA 92:1580-1584; Bell G I and Reisine T (1993) Trends Neurosci 16:34-38). Octreotide (Sandostatin$^R$) and vapreotide have a low affinity for SSTR-1, a high affinity for SSTR-2, and relatively low affinity for SSTR-3 and SSTR-5.

Somatostatin analogs have an established role in the management of patients with pituitary and neuroendocrine tumors but only a potential role in the treatment of solid tumors, including breast cancer. In this tumor type in particular, somatostatin analogs showed limited activity either when used alone or when given in combination with tamoxifen or bromocriptine. Moreover, none of the randomized trials that compared the therapeutic value of the combination of octreotide and tamoxifen versus tamoxifen alone showed any advantage in favor of combined treatment. Therefore, although the great majority of trials failed to show major side effects attributable to somatostatin analogs, the use of these compounds was limited to controlled trials (Boccardo, F. and Amoroso D. (2001) Chemotherapy 47:62-77).

The somatostatin analog called SOM230 prevents mammary gland development in rats via two mechanisms (Ruan, W et al (2006) Mol Endocrinology 20(2):426-436). One of them is an inhibitory effect on growth hormone secretion from the pituitary which can cause reduction of serum IGF-I. The other is a direct inhibition of IGF-I action in the mammary gland as demonstrated by a reduction in IRS-1 phosphorylation in the mammary gland. It has been postulated that this effect of SOM230 is mediated by either somatostatin receptor subtype (SSTR) 3 or 5 and that this causes an increase in IGF binding protein 5 (IGFBP5) which in turn blocks the local action of IGF-I in the mammary gland (Ruan, W et al (2006) Mol Endocrinology 20(2):426-436).

There is clearly a need for improved modalities and compounds for prevention of progression to breast cancer in at-risk individuals. The compound tamoxifen, which is in use for breast cancer prevention, has significant side effects due to its blocking effect of circulating estrogen. While tamoxifen is administered to antagonize estrogen action at the estrogen receptor (ER) in the breast, its systemic effects trigger signs and symptoms consistent with menopause. An alternative treatment that would provide targeted preventive therapy, without causing symptoms or signs of estrogen deficiency is therefore desired.

The citation of references herein shall not be construed as an admission that such is prior art to the present invention.

SUMMARY OF THE INVENTION

In a first aspect, a method for reducing risk of or preventing breast cancer in a mammal at risk for developing breast cancer, the method comprising: determining the number of progesterone receptor (PR)/p63 double positive (PR/p63+) progenitor cells in the mammal, wherein an elevated frequency of PR/p63+ progenitor cells in the mammal identifies the mammal as at risk for developing breast cancer, and administering to the mammal at least one inhibitor of insulin-like growth factor (IGF-I) activity to reduce the number of PR/p63+ progenitor cells in the mammal, thereby reducing risk of or preventing breast cancer in the mammal at risk for developing breast cancer. In an embodiment thereof, the number of PR/p63+ progenitor cells is determined in breast tissue of the mammal.

In a particular embodiment of the methods described herein, the mammal is a BRCA1 mutation carrier. In another embodiment, the mammal is a human.

In another embodiment of the methods described herein, the elevated frequency of PR/p63+ progenitor cells is significantly different ($p>0.05$) than that determined in a wildtype mammal. In a further embodiment, the elevated frequency of PR/p63+ progenitor cells is at least 2 times that determined in a wildtype mammal. It therefore follows that the elevated frequency of PR/p63+ progenitor cells can be at least 4, 5, 8, 10, 25, 50, 100, 500, or 1000 times that determined in a wildtype mammal. In accordance with the results presented herein, the elevated frequency of PR/p63+ progenitor cells can be at least 2 times that determined in a wildtype mammal, including any whole integer greater than 2.

In an embodiment of the methods described herein, the at least one inhibitor of IGF-I activity is an inhibitor of insulin-like growth factor I (IGF-I) or insulin-like growth factor I receptor signaling. In a particular embodiment, the at least one inhibitor is a somatostatin analog, or an antibody or small molecule inhibitor of IGF-I action on the IGF-I receptor. In a more particular embodiment, the somatostatin analog is SOM230, pasireotide/SOM230 long acting release (pasireotide LAR), somatostatin 14, SMS 201-995, BIM 23014, BIM23A779, AN-238, RC-121, cyclic somatostatin analog peptide, or somatostatin tumor inhibiting analog. Exemplary such analogs are SOM230 and native somatostatin (SS14). In a particular embodiment, a somatostatin analog preferentially targets the SSTR3 receptor and/or the SSTR5 receptor. Antibodies or small molecule inhibitors of IGF-I engagement of the IGF-I receptor that block IGF-I action in the mammary gland are also envisioned herein. Such small molecule inhibitors would be expected to block IGF-I action at all available IGF-I receptors. PQ401, for example, is a very potent and specific IGF-I receptor inhibitor.

In a further aspect of the methods described herein, administering the at least one inhibitor of insulin-like growth factor I (IGF-I) activity reduces the number of cells in the mammal comprising more than two centrosomes.

In an embodiment of the methods described herein, the frequency of PR/p63+ progenitor cells is determined in a representative tissue sample isolated from the mammal at risk for developing breast cancer. Examples of tissue samples for analysis in accordance with methods described herein include: breast cells, breast tissue, and breast biopsy tissue. Such samples can be isolated by random periareolar fine needle aspiration (RPFNA), fine needle aspiration (FNA), or any known or accepted aspiration technique involving breast tissue. Biopsies suitable for analysis as described herein include without limitation: core biopsy, excision biopsy, lumpectomy, mastectomy, reduction mammoplasty, and prophylactic mastectomy. The methods described herein benefit from the fact that only a very small biopsy sample is required for analysis.

Also encompassed herein is the use of a composition comprising an inhibitor of IGF-I activity in the mammary gland for reducing risk of or preventing breast cancer in a mammal at risk for developing breast cancer, wherein the mammal comprises an elevated frequency of progesterone receptor (PR)/p63 double positive (PR/p63+) progenitor cells and is asymptomatic for breast disease, wherein the inhibitor of IGF-I activity in the mammary gland reduces the number of PR/p63+ progenitor cells in the mammal, thereby reducing risk of or preventing breast cancer in the mammal at risk for developing breast cancer. In accordance with this embodiment, a mammal that is asymptomatic for breast disease does not exhibit clinical manifestations of breast cancer or nonproliferative cystic or fibrocystic disease. In an embodiment thereof, the mammal is a BRCA1 mutation carrier. In another embodiment, the mammal is a human. In an embodiment thereof, the inhibitor of IGF-I activity in the mammary gland is an inhibitor of insulin-like growth factor I (IGF-I) or insulin-like growth factor I receptor signaling. In a more particular embodiment, the inhibitor of IGF-I activity in the mammary gland is a somatostatin analog or an antibody or small molecule inhibitor of IGF-I action on the IGF-I receptor. In yet another particular embodiment, the inhibitor of IGF-I activity in the mammary gland is a somatostatin analog that preferentially targets the SSTR3 receptor and/or the SSTR5 receptor in the breast. As described herein, the composition may comprise a somatostatin analog selected from SOM230, pasireotide LAR, somatostatin 14, SMS 201-995, BIM 23014, BIM23A779, AN-238, RC-121, cyclic somatostatin analog peptide, and somatostatin tumor inhibiting analog.

In another aspect, a method for identifying a mammal at risk for developing breast cancer is presented, the method comprising determining the frequency of progesterone receptor (PR)/p63 double positive (PR/p63+) progenitor cells in the mammal, wherein an elevated frequency of PR/p63+ progenitor cells in the mammal identifies the mammal as at risk for developing breast cancer. In a particular embodiment, the mammal is a human. In another embodiment, the mammal is a BRCA1 mutation carrier. In an aspect thereof, the frequency of PR/p63+ progenitor cells is determined in a tissue sample isolated from the mammal. As described herein, tissue samples may include, without limitation, breast cells, breast tissue, biopsies, etc. Such samples can be isolated by random periareolar fine needle aspiration (PAFNA), fine needle aspiration (FNA), or any known or accepted aspiration technique involving breast tissue. Biopsies suitable for analysis as described herein include without limitation core biopsy, excision biopsy, lumpectomy, and mastectomy. It is noteworthy that only a very small biopsy sample is required for analysis using the methods described herein. The method may further comprise determining the frequency of cells in the mammal comprising more than two centrosomes. Also encompassed thereby is a method wherein the elevated frequency of PR/p63+ progenitor cells in the mammal is predictive of the degree of risk for developing breast cancer in a mammal.

In another aspect, a method for evaluating therapeutic efficacy of a treatment for breast cancer in a mammal is presented, the method comprising: determining the number/frequency of progesterone receptor (PR)/p63 double positive (PR/p63+) progenitor cells in the mammal at a first assessment and determining the number/frequency of PR/p63+ progenitor cells in the mammal at a second assessment, wherein the second assessment is performed after treatment onset, wherein a decrease in the number/frequency of PR/p63+ progenitor cells in the mammal at the second assessment relative to the first assessment is a positive indicator that the treatment is efficacious. In a particular embodiment, the first assessment is performed before treatment onset.

In yet another aspect, a method for identifying a cancer responsive to IGF-I inhibition is presented, the method comprising selecting a subject afflicted with a cancer, isolating a tissue sample from the subject and determining the number/frequency of progesterone receptor (PR)/p63 double positive (PR/p63+) progenitor cells in the sample, wherein an elevated frequency of PR/p63+ progenitor cells in the sample identifies the cancer as responsive to IGF-I inhibition. In an embodiment thereof, the elevated frequency of PR/p63+ progenitor cells is significantly (p>0.05) greater or at least 2 times that determined in a subject not afflicted with the cancer. In another embodiment thereof, the method further comprises treating the subject with inhibitors of IGF-I activity if the sample isolated from the subject comprises an elevated frequency of PR/p63+ progenitor cells. In yet another aspect, a method for treating breast cancer in a mammal, the method comprising administering at least one inhibitor of insulin-like growth factor I (IGF-I) activity to the mammal, wherein the at least one inhibitor is administered in accordance with an intermittent dosing regimen whereby treatment periods are interrupted by rest periods wherein the at least one inhibitor of IGF-I activity is not administered to the mammal, and the rest periods permit recovery from side effects due to administration of the at least one inhibitor of IGF-I activity. Also encompassed is the use of a composition comprising at least one inhibitor of IGF-I activity for treating breast cancer in a mammal, wherein the at least one inhibitor is administered in accordance with an intermittent dosing regimen whereby treatment periods are interrupted by rest periods wherein the at least one inhibitor of IGF-I activity is not administered to the mammal, and the rest periods permit recovery from side effects due to administration of the at least one inhibitor of IGF-I activity. In accordance with intermittent dosing regimens described herein, repetitive cycles of treatment periods and rest periods are envisioned. Thus, after completion of an initial treatment period/rest period, a second cycle of treatment period begins, to be followed by a second rest period. The number of treatment period/rest period cycles can be determined by skilled practitioners based on their assessment of the subject in need thereof, which may involve an assessment of the frequency of PR/p63+ progenitor cells in the subject. In an embodiment of the above methods and uses, an elevated frequency of PR/p63+ progenitor cells is detected in the mammal. In a particular embodiment thereof, the number of PR/p63+ progenitor cells is determined in breast tissue of the mammal. In a more particular embodiment thereof, the mammal is a BRCA1 mutation carrier. In another embodiment, the mammal is a human. In yet another embodiment of the above methods and uses, the treatment periods are 7-20 days and the rest periods range from 30-180 days. Accordingly, treatment periods may be 7, 8, 9, 10, 11, 12, 13, 14, 15, 16, 17, 18, 19, or 20 days and rest periods may be 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or 180 days.

In another embodiment of the methods and uses described herein, the elevated frequency of PR/p63+ progenitor cells is significantly different ($p>0.05$) than that determined in a wildtype mammal. In a further embodiment, the elevated frequency of PR/p63+ progenitor cells is at least 2 times that determined in a wildtype mammal. It therefore follows that the elevated frequency of PR/p63+ progenitor cells can be at least 2, 4, 5, 8, 10, 25, 50, 100, 500, or 1000 times that determined in a wildtype mammal. In accordance with the results presented herein, the elevated frequency of PR/p63+ progenitor cells can be at least 2 times that determined in a wildtype mammal, including any whole integer greater than 2.

In a further aspect of the methods and uses described herein, the at least one inhibitor of IGF-1 activity is an inhibitor of insulin-like growth factor I (IGF-I) or insulin-like growth factor I receptor signaling. In a particular embodiment, the at least one inhibitor is a somatostatin analog, or an antibody or small molecule inhibitor of IGF-I action on the IGF-I receptor. In a more particular embodiment, the somatostatin analog is SOM230, pasireotide LAR, somatostatin 14, SMS 201-995, BIM 23014, BIM23A779, AN-238, RC-121, cyclic somatostatin analog peptide, or somatostatin tumor inhibiting analog. Exemplary such analogs are SOM230 and native somatostatin (SS14). In a particular embodiment, a somatostatin analog preferentially targets the SSTR3 receptor and/or the SSTR5 receptor. Antibodies or small molecule inhibitors of IGF-I engagement of the IGF-I receptor that block IGF-I action in the mammary gland are also envisioned herein. Such small molecule inhibitors would be expected to block IGF-I action at all available IGF-I receptors. PQ401, for example, is a very potent and specific IGF-I receptor inhibitor.

Other objects and advantages will become apparent to those skilled in the art from a review of the following description which proceeds with reference to the following illustrative drawings.

BRIEF DESCRIPTION OF THE DRAWINGS

FIG. 3A-D shows the effect of SOM230 (pasireotide) on duct width (A) and (B); and on PR+/p63+ cells at 21 days post-treatment (C). Approximately 1% co-staining PR+/p63+ cells are estimated to be present at 21 days post-treatment. This percentile is expressed relative to LoxP mice which have 20% PR+/p63+ cells prior treatment, which is reduced to 5% following 7 days of SOM230 treatment. C) Immunolocalization of progesterone receptor (PR; red) and p63 (green) in the mammary glands of Brca1 deficient (loxP; Brca1$^{LoxP}$/Brca1$^{LoxP}$) mice. Nuclei (blue) are counterstained. Note that p63 and PR label distinct populations in loxP mice following SOM230 treatment, even after a 21 day rest period without treatment. D) Ki67 staining in treated and untreated loxP mice, which shows that cell proliferation continues to be inhibited at 21 days post-treatment.

FIG. 4 shows a histogram plot of duct width and the effect of SOM230 on duct width after treatment for 7 days, an effect that persists for 2 months post-treatment.

DETAILED DESCRIPTION

Figure 1A:
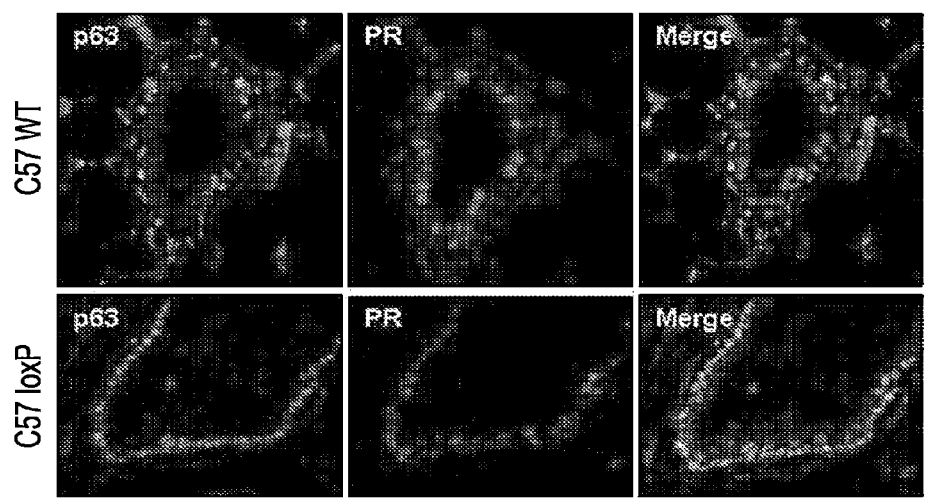
FIGS. 1A and 1B reveals that aberrant lineage commitment is eliminated by IGF-1 inhibition. A) Immunolocalization of p63 (green) and progesterone receptor (PR; red) in the mammary glands of wildtype (WT) or Brca1 deficient (loxP; Brca1$^{LoxP}$/Brca1$^{LoxP}$) mice. Nuclei (blue) are counterstained. Note that p63 and PR label distinct populations in wildtype mice, whereas Brca1 deficient mice have a population that is marked by both PR and p63. B) Quantitation of PR/p63 double positive cells shows that the frequency of these cells is reduced by 7 days pre-treatment with PQ401 or SOM230, both of which inhibit IGF-1.

There is a need for improved methods for determining breast cancer risk, particularly in those patients with a familial history of breast cancer. There is, moreover, a need for diagnostic tools with which skilled practitioners can monitor asymptomatic, high risk patients using minimally invasive techniques to assess, on an ongoing basis, risk of cancer onset. Improved diagnostic tools with which skilled practitioners can determine how best to treat a patient diagnosed with cancer are also sought. These tools can, furthermore, be applied to methods for assessing if a therapeutic regimen is efficacious for the patient. The discoveries described herein address the above-indicated long sought diagnostic, prognostic, and therapeutic needs.

Results presented herein contribute to diagnostic and therapeutic methods pertaining to diseases and disorders of the breast, uterus and ovary. More particularly, results presented herein relate to diagnostic methods for early detection of progenitor cells of breast, uterine, and ovarian cancers. The identification of markers for these previously unidentified cancer predisposing progenitor cells, which co-express the progesterone receptor (PR) and p63, provides tools and methods of use thereof for the detection early stages of cancer. More particularly, detection of increased frequency of PR/p63 double positive (PR/p63+) progenitor cells in asymptomatic patients may be used, as described herein, to identify patients in need of prophylactic regimens and to provide guidance as to which prophylactic regimen would be most efficacious. Detection of increased frequency of PR/p63+ progenitor cells in symptomatic patients provides tools and methods of use thereof for assessment, diagnostic stratification, and choice and evaluation of therapeutic intervention in these patients. Therapeutic methods are also encompassed herein, which include detection of PR/p63+ progenitor cells in a patient, wherein detection of increased frequency of PR/p63+ progenitor cells provides information on which basis a determination of therapeutic regimen can be made.

Results presented herein also demonstrate that inhibitors of IGF-I receptor activity can be used to advantage to decrease the number/frequency of PR/p63+ progenitor cells in a subject or patient and thus, provide for treatment of and/or prophylaxis for conditions and diseases of the breast, uterus, and ovary wherein increased frequency of PR/p63+ progenitor cells is detected. In a particular aspect, the invention relates to the use of compounds or agents, including somatostatin analogs, with effect on, affinity for, or specificity to SSTR3 and/or SSTR5 somatostatin receptors for the treatment of and/or prophylaxis for subjects with conditions and diseases of the breast, uterus, and ovary wherein increased frequency of PR/p63+ progenitor cells are detected. The disease may, for example, be a breast cancer wherein increased frequency of PR/p63+ progenitor cells is detected. The condition or disease may be a BRCA1 associated condition or disease of the breast (e.g., BRCA1 associated breast cancer), uterus, or ovary wherein increased frequency of PR/p63+ progenitor cells is detected. SOM230 is, for example, an exemplary somatostatin analog capable of decreasing the number of PR/p63+ progenitor cells in a subject or patient in need thereof.

Breast Cancer Risk

A variety of studies have shown that different levels of breast cancer risk can be reliably distinguished on the basis of histologic criteria in women with benign breast disease. See, for example, London et al. *JAMA* 1992, 267:941-4; Palli et al. *Int J Cancer* 1991, 47:703-6; Dupont et al. *N Engl J Med* 1985, 312:146-51; Dupont et al. Cancer 1993, 71:1258-65; Hartmann et al. *N Engl J Med* 2005, 353:229-37. Although the conclusions of these studies vary in some respects, results from the two most recent of these references are reviewed herein. The Hartmann et al. (*N Engl J Med* 2005, 353:229-37) study followed 9087 women for a median of 15 years. The histologic findings were as follows: nonproliferative lesions were noted in 67 percent of women, proliferative lesions without atypia were noted in 30 percent, and atypical hyperplasia was noted in 4 percent. At the closure of the study, 707 study participants had developed breast cancer. The relative risk of breast cancer for the cohort was 1.56 (95 percent confidence interval, 1.45 to 1.68), an increased risk that persisted for at least 25 years after biopsy. The relative risk associated with atypia was 4.24 (95 percent confidence interval, 3.26 to 5.41), as compared with a relative risk of 1.88 (95 percent confidence interval, 1.66 to 2.12) for proliferative changes without atypia and of 1.27 (95 percent confidence interval, 1.15 to 1.41) for non-proliferative lesions. A family history of breast cancer was identified as a risk factor that was independent of histologic findings. These results indicate that non-proliferative lesions are linked to an increased chance of developing breast cancer. The results of Dupont et al. (Cancer 1993, 71:1258-65) suggest that the presence of cysts (a type of non-proliferative disorder) significantly increases breast cancer risk, although this increase is largely restricted to patients with proliferative disease without atypia (PDWA). The Dupont et al. study further indicates that there is no evidence that the presence of cysts affects breast cancer risk in women without proliferative breast disease (PD) or in those with atypical hyperplasia (AH). A fourfold increase in breast cancer risk is, however, observed in women with both cysts and familial history (FH).

Fibrocystic disease of the breast is, therefore, associated with an increased risk for developing breast cancer. See Hartmann et al. (*N Engl J Med* 2005, 353:229-37), the entire contents of which is incorporated herein by reference. The increased risk is significant when coupled with proliferative disease without atypia (PDWA) or when there is a family history. See Dupont et al. (Cancer 1993, 71:1258-65), the entire content of which is incorporated herein by reference. Indeed, a fourfold increase in breast cancer risk is observed in women with both cysts and familial history (FH). See "Fibrocystic Breast Disease." *MedlinePlus*. 28 Oct. 2004. National Library of Medicine. 8 Nov. 2004 (medlineplus/ency/article/000912.htm on the world wide web nlm nih gov) and Vogel, Victor G. "Fibrocystic Breast Disease." *The Merck Manual of Medical Information*. Ed. Mark H. Beers. 2nd Home ed. Whitehouse Station, N.J.: Merck Research Laboratories, 2003. 1389-1389.

As indicated above, a reduction in the level or activities of proteins encoded by the BRCA-1 and BRCA-2 genes has been implicated in predisposition to breast, ovarian and other cancers. These proteins are ubiquitously expressed and functionally linked to a variety of essential cellular processes, including DNA repair and recombination, checkpoint control of cell cycle and transcription. Genetic susceptibility to breast cancer has, moreover, been linked to a variety of mutations of the BRCA1 and BRCA2 genes. BRCA1 mutations, moreover, account for the most common form of genetically inherited breast cancer. Women that inherit germ cell mutations of BRCA1 are at up to 80% risk of developing breast cancer and 50% risk of developing ovarian cancer.

Further to the above, inherited mutations in the BRCA1 gene predispose women to early onset breast and ovarian cancers [Alberg et al. 1997. Curr. Opin. Oncol. 9:505-511; Brody et al. 1998. Medicine (Baltimore) 77:208-226]. The BRCA1 gene includes 24 exons that encode proteins of 1,863 and 1,812 amino acids in humans and mice, respectively (Lane et al. 1995. Genes Dev. 9:2712-2722; Miki et al. 1994. Science 266:66-71.23, 27). Full-length human BRCA1 protein (BRCA1-FL) is a nuclear protein of 220 kD. Exon 11, an unusually large exon of 3.4 kb, encodes over 60% of the protein. In addition to BRCA1-FL, BRCA1 also encodes at least two protein products of smaller size due to alternative splicing (ElShamy et al. 2004. Nat. Cell Biol. 6:954-967; Thakur et al. 1997. Mol. Cell. Biol. 17:444-452; Wilson et al. 1997. Oncogene 14:1-16; Xu et al. 1999. Mol. Cell 3:389-395). One of the variants, BRCA1-Δ11 (also termed BRCA1-Δ11b), arises from in-frame splicing between exon 10 and exon 12, and retains the highly conserved amino-terminal RING finger and carboxyl-terminal BRCT domains of full-length BRCA1. The other variant is BRCA1-IRIS, which is a 1,399-residue polypeptide encoded by an uninterrupted open reading frame that extends from codon 1 of the known BRCA1 open reading frame to a termination point 34 triplets into intron 11 (ElShamy et al. 2004. Nat. Cell Biol. 6:954-967). BRCA1 has been shown to be involved in controlling genetic stability, DNA damage repair, centrosome duplication, apoptosis, and cell cycle control (reviewed in references Deng. 2002. Oncogene 21:6222-6227; Deng et al. 2003. Hum. Mol. Genet. 12:R113-R123; Venkitaraman. 2002. Cell 108:171-182; Zheng et al. 2000. Oncogene 19:6159-6175).

From a clinical standpoint, BRCA1-related tumors demonstrate distinct features with regard to histopathology (Breast Cancer Linkage Consortium. Lancet 1997; 349: 1505-1510), immunohistochemistry (IHC) (Lakhani et al. J Clin Oncol 2002; 20: 2310-2318), cytogenetics (Tirkkonen et al. Cancer Res 1997; 57:1222-1227) and gene expression profiles (Hedenfalk et al. N Engl J Med 2001; 344: 539-548; van't Veer et al. Nature 2002; 415:530-536) when compared with either non-familial breast cancer cases or BRCA2-related breast cancer. See also Osin et al. Breast Cancer Res 1999; 1:36-40; Foulkes et al. Cancer Res 2004; 64:830-835). In particular, BRCA1-related breast cancers tend to be high-grade (Lakhani et al. 2002; supra), lymph node-negative (Foulkes et al. Cancer (Phila.), 98: 1569-1577, 2003) tumors that do not express estrogen receptors (ERs), HER2 (Chappuis et al. Semin. Surg. Oncol., 18: 287-295, 2000), or the tumor suppressor gene $p27^{Kip1}$ (Chappuis et al. J. Clin. Oncol., 18:4045-4052, 2000), but do express p53 (Greenblatt et al. Cancer Res., 61: 4092-4097, 2001), cyclin E (Chappuis et al. Annals of Oncol., 16:735-742, 2005) and cytokeratin (CK) 5/6 (Sørlie et al. Proc. Natl. Acad. Sci. USA, 100:8418-8423, 2003; Foulkes et al. J. Natl. Cancer Inst. (Bethesda), 95: 1482-1485, 2003). The disclosures of all of the above cited references are incorporated herein in their entireties.

Foulkes et al. (Cancer Res 2004; 64:830-835) also analyzed data using a parsimonious multivariable proportional hazards model and confirmed that germ-line BRCA1 mutations result in breast cancers that are predisposed to be basal in character, as defined by CK5/6 IHC; and demonstrated that the basal phenotype is also characterized by large tumors that express low levels of ER, HER2, and p27Kip1 and high levels of cyclin E, and that feature both nuclear p53 and intratumoral vascular nests (GMP); all of these factors are associated with a poor outcome in univariate analysis; those tumor markers most closely linked to the basal phenotype (p53, p27Kip1, cyclin E, and GMP) are independent predictors of outcome; and the relationship between tumor size and nodal status is significantly different when comparing tumors that do, and do not, express CK5/6. The authors conclude that the basal phenotype of breast cancer deserves recognition as a separate biological entity. The combined association and survival data presented by Foulkes et al. (Cancer Res 2004; supra) suggest that much of the inferior survival after breast cancer that is experienced by BRCA1 carriers (particularly among women with lymph node-negative disease) is attributable to the basal epithelial phenotype of these cancers.

Gene expression analysis has identified several breast cancer subtypes, including basal-like, human epidermal growth factor receptor-2 positive/estrogen receptor negative (HER2+/ER−), luminal A, and luminal B. As indicated above, germline mutations in BRCA1 are associated with a significantly higher risk of developing basal-like breast cancer and are among the most aggressive. Lim et al. (Nature Medicine 2009; 15:907-913; the entire contents of which is incorporated herein in its entirety) proposed that a subset of cells thought to be luminal progenitor cells, as defined on the basis of cell surface marker expression, are targets for transformation in BRCA-1 associated basal tumors of the breast. More particularly, Lim et al. found that breast tissue isolated from BRCA1 mutation carriers comprises an expanded luminal progenitor population that exhibits factor-independent growth in vitro. The identification of a population of aberrant luminal progenitor cells in preneoplastic tissue isolated from BRCA1 mutation carriers, in combination with molecular profiling analyses, implicate luminal progenitor cells as a probable target population in BRCA-1 associated breast tumors. Luminal progenitor cells are, furthermore, suspected to be involved in other basal breast tumors as well. These findings were corroborated by Molyneux et al. (Cell Stem Cell 2010; 7:403-407; the entire contents of which is incorporated herein in its entirety) in mouse model systems of BRCA1 deficiency. More particularly, Molyneux et al. demonstrated that specifically deleting Brca1 in mouse mammary epithelial luminal progenitor cells produces tumors that phenocopy human BRCA1 breast cancers and resemble the majority of sporadic basal-like breast tumors. In contrast, directing Brca1 deficiency to basal cells produces tumors that express molecular markers of basal breast cancers, but do not resemble human BRCA1 or sporadic basal-like breast tumors histologically.

The course of BRCA1 related breast cancer is most readily observed in animal models, in part, because the disease course in human varies. In BRCA carriers, however, onset of breast cancer disease is advanced as compared to that of non-BRCA patients in whom cancer onset typically occurs in their 40s. The participation of premalignant lesions is difficult to map out in women as they have many different mutations and therefore, different, presentations. Since prophylactic mastectomy has become more common, information is now available indicating that at the time of mastectomy the prevalence of premalignant disease is high. Hoogerbrugge found that 57% of women had high risk histopathologic lesions; 37% had atypical lobular hyperplasia, 39% atypical ductal hyperplasia, 25% lobular carcinoma in situ, and 15% ductal carcinoma in situ. The women in the study were 27 to 52 years old. Some had undergone a previous mastectomy for carcinoma and were having their second breast removed. The cancer that usually develops in such women is triple negative [negative for estrogen receptors, progesterone receptors, and human epidermal growth factor receptor 2 (HER2)]. The same pattern is observed in the animal models.

To further investigate BRCA1 associated disease, scientific research has focused on studying animal models of Brca1 deficiency. Unfortunately, mice homozygous for point mutations of Brca1 die in utero. For that reason investigators have turned to conditional deletions of the main exon of Brca1 (exon 11) by a Cre-LoxP approach (Xu et al. 1999, Nature Genetics 22:37-43). This makes the animals deficient in the full length BRCA1 protein. This serves as an acceptable model in some respects, but the model is limited in that mammary tumor formation occurs only after long latency. More particularly, Xu et al. demonstrate that in this model system, no tumor formation is observed in 2-20 month old mice. Mammary tumors were eventually observed in 10-13 month old mice. Moreover, breeding is difficult and this makes difficult the testing of large numbers of animals. Accordingly, the animal model system disclosed by Xu et al. is limited with respect to understanding BRCA1 associated disease in human patients, at least in part because the system fails to recapitulate the typical early onset pattern of disease manifestation observed in human BRCA1 carriers. By way of comparison, a comparative timeline of human lifespan and typical onset of disease manifestation in BRCA1 carriers as compared to that determined for the BRCA1 conditional mutant mice described by Xu et al. reveals that the onset of disease in BRCA1 conditional mutant mice described by Xu et al. occurs at an advanced age.

Kim et al. (Mol Cell Biol 2006, 26:6983-6992) have developed a different BRCA1 mutated animal model that is deficient in the BRCA1 protein obtained by alternative splicing of Exon 11 (BRCA1 Δ11). In addition to developing late onset breast carcinoma, these animals have abnormalities in mammary ducts and have many areas of hyperplasia. They also have uterine and ovarian abnormalities. Like Xu et al., Kim et al. report that female mice exhibit mammary gland abnormalities and uterine hyperplasia with spontaneous tumor formation, but only after a year of age. The animal model system disclosed by Kim et al. is, therefore, also limited with respect to understanding BRCA1 associated disease in human patients, at least in part because the system fails to recapitulate the typical early onset pattern of disease manifestation observed in human BRCA1 carriers.

LoxP Animal Model System

In the process of developing animals with a conditional deletion of exon 11, it was determined that mice with loxP sites flanking exon 11 (LoxP animals), before being crossed with MMTV-Cre carriers, exhibit an extreme phenotype of the mammary glands and the uteri. The mammary glands of LoxP mice have dilated ducts and areas of dysplasia and hyperplasia. By the age of 4 months, HAN-like lesions (abnormal preneoplastic lesions) are observed in these animals. Hyperplastic dilated uteri are also noted in LoxP mice. The term $Brca1^{LoxP}/Brca1^{LoxP}$ mice is used interchangeably herein with "LoxP" mice and each of these terms refers to the same strain of mice.

By 28 days of age, LoxP animals begin to exhibit developmental abnormalities and these continue until at least 9 months. More particularly, by two months of age, the mammary gland phenotype in $Brca1^{LoxP}/Brca1^{LoxP}$ and C57Bl/6 control mice are phenotypically distinct. $Brca1^{LoxP}/Brca1^{LoxP}$ mice have terminal end buds, a sign of ongoing mammary development, whereas control mice lack such features. No ductal or lobular hyperplasia, however, is observed in two month old $Brca1^{LoxP}/Brca1^{LoxP}$ mice. Another notable phenotypic distinction observed in two month old $Brca1^{LoxP}/Brca1^{LoxP}$ mice is the presence of enlarged ducts, which are not apparent in age matched C57Bl/6 control mice. The peak ductal width abnormality occurs at 4 months of age in $Brca1^{LoxP}/Brca1^{LoxP}$ mice, while the prevalence of hyperplastic lesions increases with age.

For comparative purposes to a human lifespan, two month old mice are in late puberty and four month old mice are adults. Accordingly, the early onset of abnormalities that present in $Brca1^{LoxP}/Brca1^{LoxP}$ mice are interesting in several respects. The early onset of the phenotype of non-proliferative cystic lesions in $Brca1^{LoxP}/Brca1^{LoxP}$ mice, as evidenced by ductal dilation, facilitates examination of phenotypic risk factors that appear earlier in life, in advance of benign hyperplastic disease onset. The appearance of non-proliferative cystic lesions in $Brca1^{LoxP}/Brca1^{LoxP}$ mice appears to recapitulate aspects of early disease onset believed to occur in BRCA1 associated disease in humans. No one has performed a study of the age at which such lesions occur in BRCA1 mutated patients, but almost 40% of BRCA1 patients have such lesions by the time they have elected to have prophylactic mastectomies, and breast cancer in BRCA1 patients can appear in the early 20s.

Moreover, although the phenotype of two month old $Brca1^{LoxP}/Brca1^{LoxP}$ mice is profoundly abnormal, it is less cystic than that observed in four month old $Brca1^{LoxP}/Brca1^{LoxP}$ mice and does not have areas of atypical hyperplasia characteristic of the four month old animals. These results suggest that there is a temporal cascade of hyperactive mammary development, including ductal dilation (cystic disease), that develops by late puberty in $Brca1^{LoxP}/Brca1^{LoxP}$ mice (at two months) and evolves into a phenotype of greater duct dilation and the beginning of atypical hyperplasia, as observed in adult $Brca1^{LoxP}/Brca1^{LoxP}$ mice (at four months). As $Brca1^{LoxP}/Brca1^{LoxP}$ mice age as adults, the ducts fail to enlarge further and may indeed decrease in size, while atypical hyperplasia reaches a maximal level. These findings support a progression from non-proliferative cystic disease of the breast to cystic disease in combination with atypical hyperplasia, which in turn, leads to malignant breast cancer. This progressive cascade from non-proliferative cystic disease of the breast, to cystic disease in combination with atypical hyperplasia, to malignant breast cancer clearly applies to human BRCA1 carriers and likely applies to patients with highly symptomatic fibrocystic disease which consists of breast lumps and breast pain and tenderness.

The early phenotypic changes observed with the $Brca1^{LoxP}/Brca1^{LoxP}$ (LoxP) animal model system used herein strongly suggest that this is a valid model system for further investigations directed to understanding BRCA1 associated disease in human patients, at least in part because the system recapitulates the typical early onset pattern of disease manifestation observed in human BRCA1 carriers. It also applies to human patients with highly symptomatic fibrocystic disease who may be at higher risk of developing breast cancer.

Additional characterization of the LoxP animal model system revealed that a significant difference in levels of Brca1 Δ11 mRNA, as assayed by either qualitative or quantitative RT-PCR, is not observed in the LoxP animals when compared to controls. In contrast, the expression of the Δ11 protein was decreased in comparison to wild type animals. In contrast, the full length protein is expressed similarly in controls and LoxP animals. These results suggest that the phenotypic changes observed in the LoxP animal model system are at least in part due to impaired expression of Brca1 Δ11.

Although not wishing to be bound by theory, the phenotypic changes observed in the LoxP animal model system also appear to be due at least in part to the presence of the LoxP sites in the full length (FL) BRCA1 transcript. This assertion is made based on several lines of reasoning, including the fact that 1) when crossed with MMTV cre, which results in removal of the LoxP sites and intervening exon 11, the phenotype of the LoxP animals is reduced; 2) when crossed to wildtype animals, the phenotype of the LoxP animals is reduced; and 3) the phenotype described by Kim et al., wherein only FL BRCA1 is made in an animal model system, is far less severe than that observed in the LoxP animal model system described herein, wherein only the FL BRCA1 protein is made, but it includes LoxP sites.

As a consequence of the above, it is reasonable to suggest that the phenotypic presentation of the LoxP animal genotype reflects a "double hit" to the BRCA1 proteins, whereby not only is the expression of the Brca1 Δ11 truncated form of BRCA1 impaired, but the activity of FL BRCA1 is altered and/or impaired by the presence of at least one of the LoxP sites. Again, although not wishing to be bound by theory, the impaired activity of FL BRCA1 could be due to generally altered activity (e.g., tumor suppressor activity) of the FL BRCA1 FL transcript due to the presence of at least one of the LoxP sites; impaired nuclear localization of the FL BRCA1 due to the presence of at least one of the LoxP sites, and/or altered interaction with other cellular components that interact directly or indirectly with the FL BRCA1 wild type protein due to the presence of at least one of the LoxP sites.

Further to the above, the LoxP animal model resembles, in some respects that of systems wherein expression of full length BRCA1 is impaired (Skukla et al. 2006, Cancer Res 66:7151-7157). Like those of mice homozygous for targeted deletion of full length BRCA1, the mammary glands of LoxP animals have increased IGF-I activity as measured by phosphorylation of IGF-IR and its downstream mediators ERK and AKT.

The present inventor and colleagues have previously shown that growth hormone induced IGF-I activity is essential for mammary development and also estrogen and progesterone action. To determine whether inhibition of IGF-I action would prevent, reverse or delay the abnormalities associated with BRCA deficiency observed in LoxP animals, symptomatic animals were treated with three different compounds that inhibit IGF-I action. Pasireotide, for example, has been shown by the present inventor and colleagues to inhibit IGF-I action in the mammary gland (Ruan et al. 2006, Mol Endocrinol 20:426-436. Pasireotide is a somatostatin analog that binds to 4 of the 5 somatostatin receptors. Somatostatin 14 (SS14), which binds to all of the somatostatin receptors, and an IGF-I receptor blocker (PQ401) were also utilized. The latter two are both available commercially, whereas the pasireotide is a product of Novartis. Each one of these drugs is effective in reversing or preventing the LoxP mammary phenotype. In sum, each of these drugs reduces duct width, glandular hyperplasia and hyperplastic alveolar nodules and tends to normalize the architecture of the mammary glands. Both pasireotide and PQ401 also significantly reduce cell proliferation as assessed by Ki67 immunohistochemistry. Prevention or reversal of the phenotype and impressive reduction in the number of HANs was observed following treatment of nine month old animals with SS14.

As shown herein, the LoxP animal model system is also useful for assaying the efficacy of inhibitors of IGF-I activity in the prevention and/or treatment of cancer in patients having a genetic predisposition to cancer, wherein increased frequency of PR/p63 double positive (PR/p63+) progenitor cells is detected. This is particularly relevant with respect to asymptomatic patients having a genetic predisposition to a cancer, such as, for example, cancer of the breast, uterus, or ovary. The LoxP animal model system is, furthermore, useful for assaying the efficacy of inhibitors of IGF-I activity in the prevention and/or treatment of breast cancer, cystic disease of the breast and hyperplastic disorders of the breast, wherein increased frequency of PR/p63+ progenitor cells is detected. As further described herein, hyperplastic disorders of the breast include: usual hyperplasia, intraductal papilloma, fibrocystic disease, atypical ductal hyperplasia, and atypical lobular hyperplasia. In a particular aspect, the hyperplastic disorder involves precancerous and/or cancerous lesions in BRCA1 mutation carriers, wherein increased frequency of PR/p63+ progenitor cells is detected. In a more particular aspect, the LoxP animal model system is useful for assaying the efficacy of IGF-I inhibitors in the prevention of cancer in BRCA1 mutant carriers, wherein increased frequency of PR/p63+ progenitor cells is detected.

Breast Cancer Progenitor Cells

Recent studies indicate that BRCA1 mutation perturbs epithelial lineages and allows the expansion of the luminal progenitor population. Dysregulated stem cell number is speculated to lead to tissue hyperplasia via stem cell hyperproliferation and eventually to tumorigenesis (Morrison et al. Nature 2006; 441:1068-74; Wright et al. Breast Cancer Res 2008; 10:R10). Basal-like breast cancers arising in women carrying mutations in the BRCA1 gene are thought to develop from mammary stem/progenitor cells (Wright et al. Breast Cancer Res 2008; 10:R10; Burga et al. Cancer Res 2009; 69:1273-8). Knockdown of BRCA1 in primary breast epithelial cells leads to an increase in cells displaying ALDH1 and a decrease in cells expressing luminal epithelial markers and estrogen receptor (Liu et al. Proc Natl Acad Sci USA 2008; 105:1680-5). In breast tissues, loss of heterozygosity for BRCA1 is observed in ALDH1-positive lobules but not in adjacent ALDH1-negative lobules, which suggests that the loss of BRCA1 function blocks epithelial lineage commitment of ER-positive cells. A study by Lindeman and colleagues identified a luminal progenitor cell using surface markers and provides evidence suggesting that these ER-negative cells are expanded in BRCA1 mutation carriers (Lim et al. Nature Med 2009; 15:907-13). Likewise Smalley and colleagues have now shown that Brca1 transformation of luminal progenitors induces basal-like tumors (Molyneux et al. Cell Stem Cell 2010; 7:403-17).

The breast epithelium consists of two cell layers, luminal and basal. Luminal epithelial cells generally respond to ovarian steroid hormones, estrogen and progesterone intermittently made in the ovaries as a function of the menstrual cycle and pregnancy, by undergoing cell division or secretory differentiation. These events are induced by their cognate receptors, PR and ER. These receptors are hormone binding proteins that are distributed in cells of the epithelium of the breast and uterus. PR is regulated by ER, whose ligand is estrogen, in a fashion to coordinate proliferation and differentiation of breast in preparation for milk production. The ligand for PR is progesterone. PR is expressed in a portion of differentiated luminal epithelial cells and is thought to mediate epithelial proliferation.

The basal layer of the breast epithelium consists predominantly of myoepithelial cells whose main function is contraction during lactation. p63 is expressed predominantly in basal breast cells. p63 protein is a transcription factor that can regulate a wide spectrum of target genes. p63 is critical for the development of stratified epithelial tissues such as epidermis, breast, and prostate. p63 is also implicated in tumor formation and progression in stratified epithelia, with evidence for both tumor suppressive and oncogenic properties. Humans in which P63 is mutant do not develop breasts. Stem and progenitor cells are thought to be located in a basal or suprabasal position in the breast epithelium. Several studies have implicated p63 as a critical signal and/or marker of stem cells.

As described herein, the present inventors discovered that Brca1$^{LoxP}$/Brca1$^{LoxP}$ deficient mice contain a significantly expanded population of cells co-expressing progesterone receptor (PR) and p63. Brca1$^{LoxP}$/Brca1$^{LoxP}$ mice also exhibit centrosome abnormalities that give rise to genomic instability. These features are known to increase the risk of developing cancer. These findings revealed the identity of a population of PR/p63 double positive progenitor cells, detection of which in a subject can be used for a variety of purposes, including diagnostic and prognostic assessments.

Figure 1B:
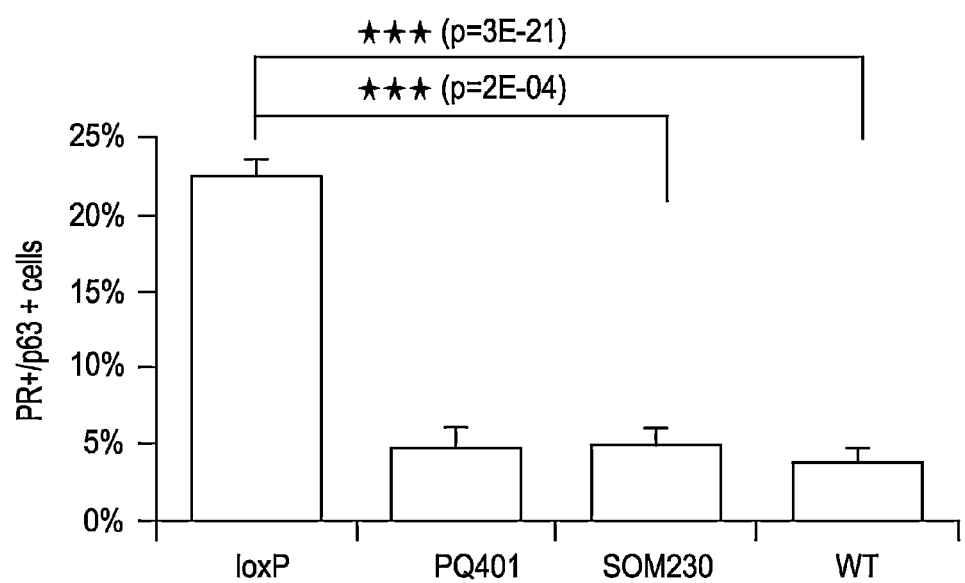

More particularly, FIG. 1 shows that aberrant lineage commitment is eliminated by treatment with inhibitors of IGF-I activity. FIG. 1A shows immunolocalization of p63 (green) and progesterone receptor (PR; red) in the mammary glands of wildtype (WT) or Brca1 deficient (loxP; Brca1$^{LoxP}$/Brca1$^{LoxP}$) mice. The nuclei (blue) are counterstained. It is noteworthy that p63 and PR label distinct populations in wildtype mice, whereas Brca1 deficient mice comprise an expanded population that is labeled for both PR and p63 (PR+/p63+ double positive cells). FIG. 1B shows quantitation of PR/p63 double positive cells, revealing that the frequency of these cells is dramatically reduced by 7 days of treatment with PQ401 or SOM230, both of which inhibit IGF-I activity. Treatment with either of PQ401 or SOM230 essentially reduces the number of PR/p63 double positive cells to that of wildtype mice, demonstrating reversion of the aberrant cellular population phenotype observed in the Brca1 deficient mice.

Figure 2A:
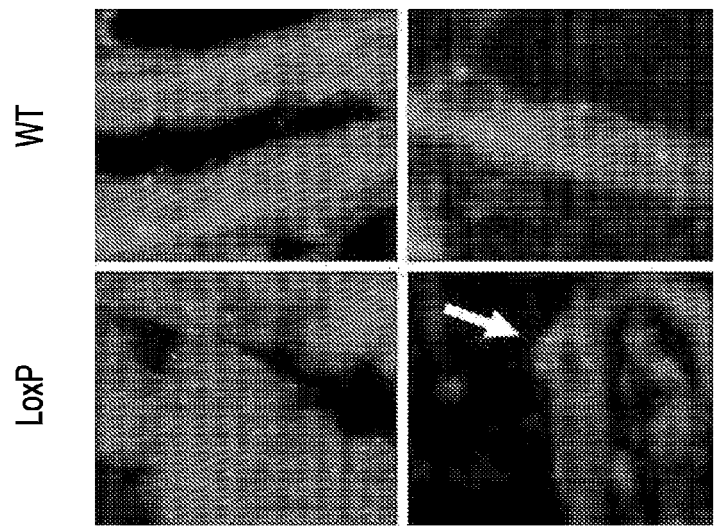
FIGS. 2A and 2B shows that genomic instability is eliminated by IGF-1 inhibition. A) Immunolocalization of γ-tubulin (green) and to locate centrosomes in the mammary glands of wildtype (WT) or Brca1 deficient (loxP; Brca1$^{LoxP}$/Brca1$^{LoxP}$) mice. Nuclei (blue) are counterstained. Note that only 1 or 2 centrosomes per cell is normal, as is predominant in wildtype mice, whereas Brca1 deficient mice have a population of cells that has significantly more than 1 or 2 centrosomes per cell (white arrow). B) Quantitation of centrosome index (normal equals 1) shows that the frequency of these cells is reduced by 7 days pre-treatment with PQ401 or SOM230, both of which inhibit IGF-1.
Figure 2B:
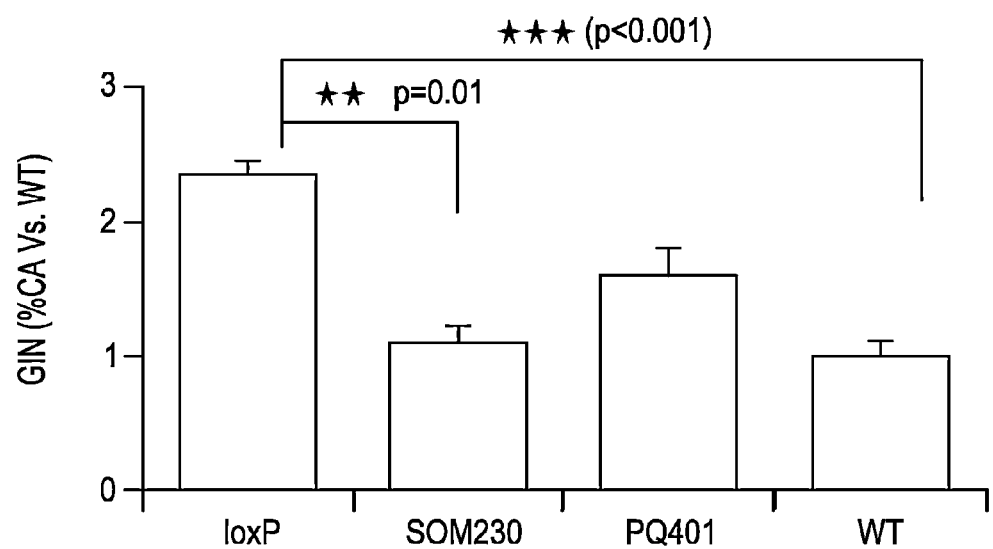

FIG. 2 reveals that treatment with inhibitors of IGF-I activity dramatically reduces the level of genomic instability observed. Indeed, the number of cells exhibiting genomic instability in Brca1$^{LoxP}$/Brca1$^{LoxP}$ mice following IGF-I inhibitor treatment is essentially reduced to that observed in wildtype animals. Evidence directed to this point is presented in FIG. 2A, wherein immunolocalization of γ-tubulin (green) is used to locate centrosomes in the mammary glands of wildtype (WT) or Brca1 deficient (Brca1$^{LoxP}$/Brca1$^{LoxP}$) mice. Nuclei (blue) are counterstained. As shown therein, 1 or 2 centrosomes per cell are observed in wildtype mice, reflecting normal, control numbers of centrosomes in individual cells. In contrast, LoxP mice comprise a population of cells that have significantly more than 1 or 2 centrosomes per cell (white arrow indicates an exemplary cell in this population). FIG. 2B shows a graph depicting quantitation of the centrosome index (normal equals 1) for wildtype (normal control) and LoxP mice, which analysis reveals that the frequency of these cells is significantly reduced by 7 days of treatment with PQ401 or SOM230, both of which inhibit IGF-1 activity.

FIG. 3 shows that treatment with inhibitors of IGF-I activity reduces duct width, the number of PR+/p63+ cells, and the number of proliferative cells in LoxP mice and, moreover, demonstrates that the effect persists post-treatment. FIG. 3B, for example, shows that SOM230 (pasireotide) treatment reduces duct width and this effect is maintained even 21 days post-treatment. The number of PR+/p63+ cells in LoxP mice is also reduced from 20% PR+/p63+ cells prior to SOM230 treatment to 5% following 7 days of SOM230 treatment. Evidence as to the persistence of this effect is detectable via immunolocalization at 21 days post-treatment with SOM230, which reveals that only approximately 1% co-staining PR+/p63+ cells are present at this stage of the rest period. Indeed, no PR+/p63+ cells are present in the panels shown in FIG. 3C which depict the number of these cells in loxP mice after a 21 day rest period post SOM230 treatment. The results depicted in FIG. 3D show Ki67 staining in treated loxP mice at 21 days post-treatment and untreated LoxP mice. Cell proliferation, for which Ki67 staining serves as an indicator, is inhibited even 21 days into the rest period.

FIG. 4 shows a histogram plot of duct width and the effect of SOM230 on duct width after treatment for 7 days. The reduction in duct width clearly persists for at least 2 months post-treatment.

Figure 5:
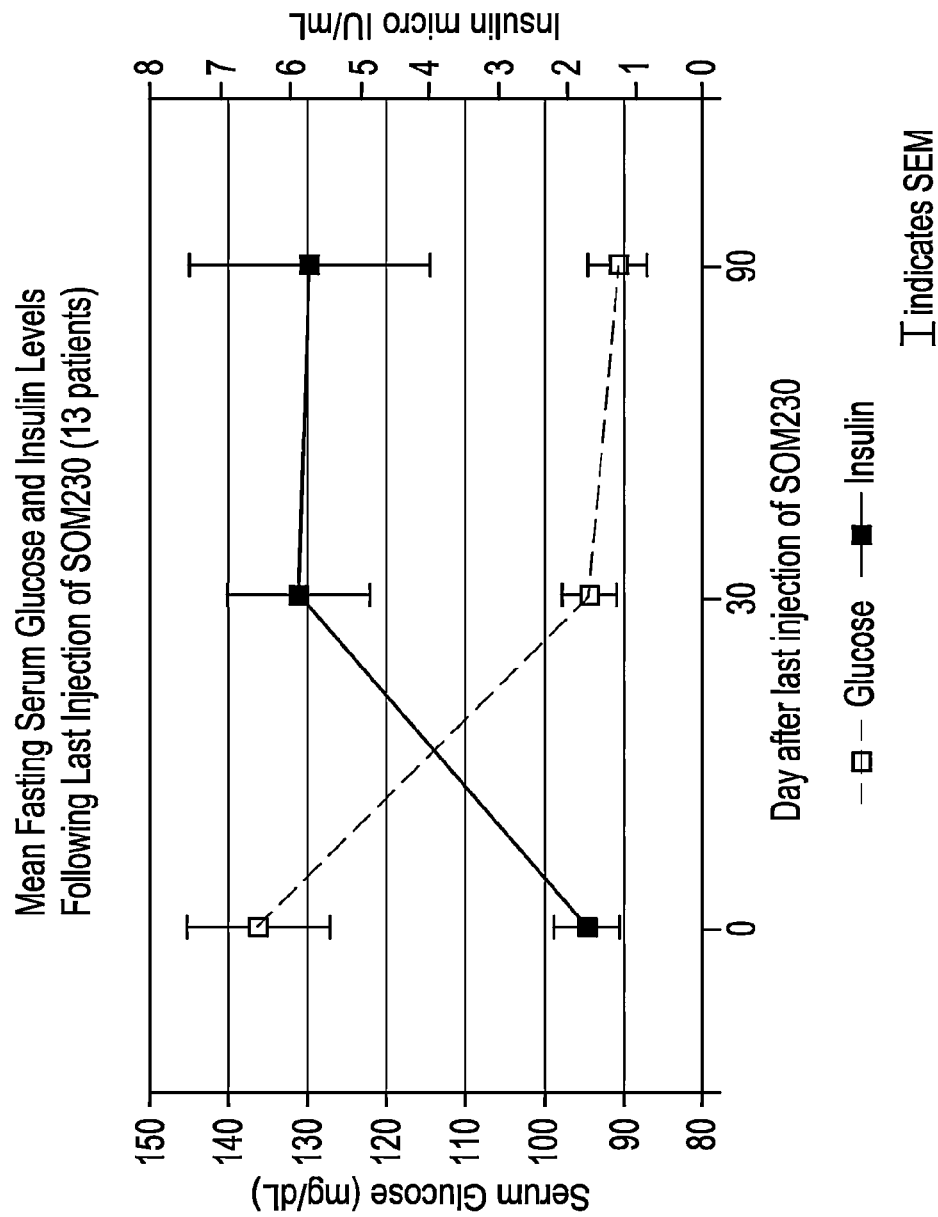
FIG. 5 is a graph showing serum glucose and insulin levels during SOM230 treatment and post SOM230 treatment. The results are based on analyses of 13 patients treated with SOM230. By 30 days post SOM230 treatment (after stopping SOM230), mean glucose was 95 and serum insulin was increased. Both continued to be normal at 60 days after discontinuation.

FIG. 5 is a graph showing serum glucose and insulin levels post SOM230 treatment. The results are based on analyses of 13 patients treated with SOM230. The serum glucose and insulin levels normalize by 30 days after SOM230 administration ceases. The glucose levels fall as the insulin levels are restored following cessation of treatment. By 4 days after cessation of SOM230 administration, 6 of 8 of the women tested had finger stick glucoses of less than 92 mg/dL. Given these findings, it is apparent that glucose levels normalize soon after SOM230 administration ceases.

One of the patients in the analysis was, however, ultimately determined to be diabetic, even though her initial blood sugar level was 100. Her 30 day post-treatment glucose was 117. It was notably lower than during SOM230 administration, but was not normal.

As shown herein, both SOM230 (pasireotide) and PQ401 significantly reduce the number of aberrant cells in the mammary glands of these animals. In light of these results, the present inventors have identified novel in situ markers of aberrant lineage commitment and shown that this specific population can be significantly inhibited by blocking IGF-I action by two different agents (pasireotide and PQ401).

In accordance with results set forth herein, the present inventors have discovered a population of PR/p63 double positive (PR/p63+) progenitor cells, increased frequency of which relative to wildtype controls serves as an in situ marker for increased risk of cancer.

Accordingly, detecting increased frequency of PR/p63+ progenitor cells in situ for a subject can be used as a diagnostic tool to predict cancer risk; detect onset of early, asymptomatic stages of a cancer; evaluate therapeutic regimens for treatment of a patient with a cancer; and evaluate prophylactic regimens for the reduction of risk of a cancer in a subject at risk for developing the cancer. Such prophylactic regimens may be used to delay or, optimally prevent cancer onset in such subjects. With respect to treatment of subjects/patients with cancer, the cancer may be breast, ovarian, uterine, or prostate cancer. With respect to treatment of subjects/patients with a disease or disorder that is a benign disease, such a disease or disorder may be non-proliferative cystic or fibrocystic disease of the breast. This analysis could be performed on small amount of tissue readily obtained in primary or sequential biopsy, in contrast to prior work in which large amounts of tissue were disaggregated and selected cells analyzed using flow cytometry of cell surface markers that discriminate progenitor populations and distribution of cell lineages.

Accordingly, the present inventors envision that the findings presented herein could immediately lead to determining whether inhibitors of IGF-I activity can be used to eliminate the cells that are predisposed to become cancer and eliminate those with genomic instability. The present findings also suggest that subjects (men or women) afflicted with a breast cancer not associated with BRCA1 mutations might be potential candidates for treatment with IGF-I inhibitors to prevent or treat the breast cancer if increased frequency of PR/p63+ progenitor cells is observed in these subjects. This application of the results presented herein is based, in part, on the prediction that the Brca1 deficient animal models described herein are extreme examples of spontaneous breast cancer.

The present inventors, furthermore, envision that the results presented herein may, for example, be applied advantageously with respect to reducing the risk of developing breast cancer for patients in which increased frequency of PR/p63+ progenitor cells is detected; reducing the risk of other cancers in which genomic instability is a mechanism; use as tools to evaluate experimental models for similarities to human breast biology; use as tools to evaluate experimental therapies for reducing the risk of developing breast cancer; use as prognostic markers for women at high risk for developing breast cancer (e.g., BRCA1 mutations); use as diagnostic markers for identifying women with a predisposition for developing breast cancer; use as diagnostic markers for other tissues which are sensitive to IGFI in cancer development (e.g., prostate); and therapy for potential treatment of subjects afflicted with breast cancer, wherein increased frequency of PR/p63+ progenitor cells is detected.

The present inventors have found that the therapeutic effects of selected IGF-I inhibitors, as exemplified by SOM230 (pasireotide), have long lasting, persistent effects whereby the clinical benefit, as measured by a reduction in the number of PR/p63+ progenitor cells, ductal width, and/or number of proliferative cells, is maintained well past the time at which administration of the inhibitor of IGF-I activity ends. As described herein, the term "rest period" refers to that period of time after which administration of the inhibitor of IGF-I activity ends or ceases. Accordingly, rest period refers to a time frame post-treatment. As described herein, the clinical benefit, as measured by a reduction in the number of PR/p63+ progenitor cells, ductal width, and/or number of proliferative cells, is maintained for at least 20 days into the rest period. See, for example, FIG. 3. Indeed, as shown in FIG. 4, the SOM230-mediated reduction in ductal width is maintained for at least 2 months into the rest period.

Given the plasma half life of SOM230 of approximately 12 hours in humans, as determined by Ma et al. (Clin Pharmacol Ther 78:69-80, 2005) and the terminal half life of SOM230 in humans and rats of 27 hours as determined by Bruns et al. (Eur J Endocrinol 146:707-716, 2002) and van der Hoek et al. (J Clin Endocrinol & Metabolism 89:638-645, 2004), the findings of the present inventors are surprising. Further to this point, U.S. Pat. No. 7,473,761 (Albert et al.), which describes the structure of SOM230 and basic structural and pharmacological properties thereof, indicates that SOM230 has an elimination half-life between 15 and 30 hours. In keeping with these findings, Albert et al. discloses general dosing parameters that range from once to thrice per day. All of the above disclosures reflect the state of the art with respect to the half life of SOM230 and underscore that there would have been no reason for an ordinarily skilled practitioner to expect that SOM230 could confer lasting effects. Indeed, the therapeutic regimens used, particularly those established for clinical trials, reflect the understanding in the field that SOM230 should be dosed daily, twice daily, or even continuously to confer therapeutic benefit. Typical dosing for human subjects is described in, for example, Boscaro et al. (J Clin Endocrinol Metabol 94:115-122, 2009), wherein patients with pituitary-dependent Cushing's disease self-administered pasireotide (SOM230) subcutaneously (sc) at a dose of 600 μg bid for 15 days; Farrall et al. (Presented at ENDO 2007 abstract OR53-4; see also Schmid Molec & Cell Endocrin 286:69-74, 2008), wherein patients with active acromegaly were treated in a Phase II randomized open label crossover study with SOM230 doses of 200, 400, and 600 μg sc bid after an initial treatment of octreotide at 100 μg sc three times a day (tid) for 28 days; and Kvols et al. (J Clin Oncol. 24:4082, 2006), wherein the safety and efficacy of pasireotide (SOM230), administered initially at 300 μg and escalated to a maximum of 1200 μg sc bid every 3 days until clinical response was achieved, was evaluated in a phase II study in patients with metastatic carcinoid tumors refractory or resistant to octreotide LAR.

The state of the art is also reflected in the dosing regimens used in animal studies. Weckbecker et al. (Endocrinology 143:4123-4130, 2002), for example, describe administering SOM230 continuously via osmotic pump to rats, monkeys, and beagles. Fedele et al. (Clin Cancer Res 13:2738-2744, 2007) disclose continuous sc injection of SOM230 at different doses to HMGA2 transgenic mice, which develop growth hormone/prolactin-secreting pituitary adenomas and thus serve as an animal model system for human pituitary adenoma. Castillo et al. (Neuroendocrinology 94:124-136, 2011), moreover, describe treating dogs with Cushing's disease with SOM230 sc every 12 hours continuously for months. Accordingly, both human and animal studies have been performed in a manner consistent with an apparent need for SOM230 administration with some frequency, such frequency being at least once daily, if not continuously.

In view of the above, the findings of the present inventors, which demonstrate that clinical benefit of SOM230 treatment remains well into a rest period (period following cessation of treatment) indicate that previously unappreciated intermittent dosing regimens for administering SOM230 to subjects in need thereof, including human subjects, may confer maximum benefit to such subjects, while minimizing adverse side effects that manifest particularly during active treatment phases. Adverse side effects that result from SOM230 administration, as described by Colao et al. N (Engl J Med 366:914-924, 2012) in a Phase III study of Cushing's disease include diarrhea (58%), nausea (52%), hyperglycemia (40%), and cholelithiasis (30%). Fasting plasma glucose and HbA1C levels also increased as a consequence of SOM230 treatment and 73% of patients had a hyperglycemia-related adverse event. See also Fleseriu et al. (Pituitary, published online Jun. 7, 2012; DOI 10.1007/s11102-012-0397-5). The present inventors also observed hyperglycemia in 100% of the patients treated with SOM230 who had either been diagnosed with breast cancer or who were pre-disposed to breast cancer. More particularly, the women identified as pre-disposed or at higher risk than the average woman for developing breast cancer, had proliferative lesions that significantly increase the risk of breast cancer. Such proliferative lesions include typical forms of hyperplasia that may increase cancer risk, or atypical lesions that increase the risk five-fold relative to that of the average woman. See, for example, FIG. 5 which affirms that hyperglycemia is a common side effect of patients treated with SOM230. FIG. 5 also shows that reversion of elevated glucose after discontinuing SOM230 is rapid. Indeed, finger stick glucose measurements show that normalization of glucose happens almost immediately after stopping medication. Accordingly, the present inventors demonstrate herein that hyperglycemia, a serious side effect of SOM230 administration, can be corrected rapidly, and without further intervention, following discontinuation of SOM230, while the therapeutic benefits of SOM230 administration are persistent. See, for example, FIGS. 3-5. As described herein, the therapeutic benefit of SOM230 persists as measured by a decrease in the frequency of abnormal PR/p63+ progenitor cells, a decrease in the number of cells with more than two centrosomes, or a reduction in ductal width or any combination thereof. That being the case, the present inventors have devised a therapeutic regimen based on their surprising results that calls for intermittent dosing of SOM230 to subjects/patients in need thereof.

It is also noteworthy that the results presented herein demonstrate an almost immediate reversion from elevated glucose and low insulin levels to normal levels of both and yet, reveal that the beneficial effects of SOM230 treatment on reducing the frequency of abnormal PR/p63+ progenitor cells persist. Although not wishing to be bound by theory, these results suggest that the effect of SOM230 with respect to reducing the frequency of abnormal PR/p63+ progenitor cells is at least partially independent of SOM230's effects on pathways that regulate glucose levels.

As used herein, the term "cystic disease", or "fibrocystic disease" of the breast refers to a benign disease common in women in their thirties, forties and fifties, marked by small fluid containing cysts that form in one or both breasts and associated with stromal fibrosis and varying degrees of intraductal epithelial hyperplasia and sclerosing adenosis.

As used herein, the term "non-proliferative cystic disease", or "non-proliferative fibrocystic disease" of the breast refers to a benign disease common in women in their thirties, forties and fifties, marked by small fluid containing cysts that form in one or both breasts and associated with stromal fibrosis, and lacking detectable regions of hyperplasia.

As used herein, "highly symptomatic fibrocystic disease" is characterized by the presence of breast lumps and breast pain and tenderness. In the absence of detectable regions of hyperplasia, the term "highly symptomatic non-proliferative fibrocystic disease" may be used to define a patient population for treatment as described herein. Use of agents and/or compositions as described herein to alleviate symptoms associated with "highly symptomatic non-proliferative fibrocystic disease" is also encompassed herein.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-Ill [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "somatostatin analog(s)", "SST analogs", "somatostatin" and any variants not specifically listed, may be used herein interchangeably, and as used throughout the present application and claims refer to proteinaceous material including single or multiple proteins or non-proteinaceous materials, and extends to those proteins having somatostatin or somatostatin-like activities, including the ability to bind to and/or otherwise modulate one or more somatostatin receptors SSTR1-SSTR5. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "somatostatin analog(s)", "SST analogs", "somatostatin" are intended to include within their scope proteins specifically recited herein as well as all substantially homologous analogs and allelic variations.

Somatostatins bind somatostatin receptor(s), with subtypes SSTR-1 to SSTR-5 identified, cloned, and functionally characterized (Patel et al (1995) Life Sci 57:1249-1265; Patel Y C et al (1996) Metabolism 45 (suppl 1):31-38; Reisine T and Bell G I (1995) Endocrin Rev 16:427-442; Buscail L et al (1995) PNAS USA 92:1580-1584; Bell G I and Reisine T (1993) Trends Neurosci 16:34-38). Octreotide and vapreotide have a low affinity for SSTR-1, a high affinity for SSTR-2, and moderate affinity for SSTR-3, SSTR-4 and SSTR-5.

The somatostatin analog SOM230 prevents mammary development in rats via two mechanisms (Ruan et al (2006) Mol Endocrinology 20(2):426-436). One of them is an inhibitory effect on growth hormone secretion from the pituitary which can cause reduction of serum IGF-I. The other is a direct inhibition of IGF-I action in the mammary gland as demonstrated by a reduction in IRS-1 phosphorylation in the mammary gland. It has been postulated that this effect of SOM230 is mediated by either somatostatin receptor subtype (SSTR) 3 or 5 and that this causes an increase in IGF binding protein 5 (IGFBP5) which in turn blocks the local action of IGF-I in the mammary gland (Ruan et al (2006) Mol Endocrinology 20(2):426-436). Somatostatin analog SOM 230 is the subject of U.S. Pat. No. 7,473,761 (corresponding to PCT/EP01/08824, published as WO 02/01092A3; priority Aug. 1, 2000). U.S. Pat. No. 7,473,761 describes the compound, compositions thereof, and method of preventing or treating disorders with an etiology comprising or associated with excess GH-secretion and/or excess IGF-1, the entire contents of which is incorporated herein in its entirety. SOM230 (pasireotide) is a multireceptor-targeted somatostatin analog with high binding affinity for SSTR1, 2, 3, and 5 (Schmid et al. J Endocrinol 2012 January; 212(1):49-60. Epub 2011 Oct. 10).

As described therein, the structure of SOM230 is as follows:

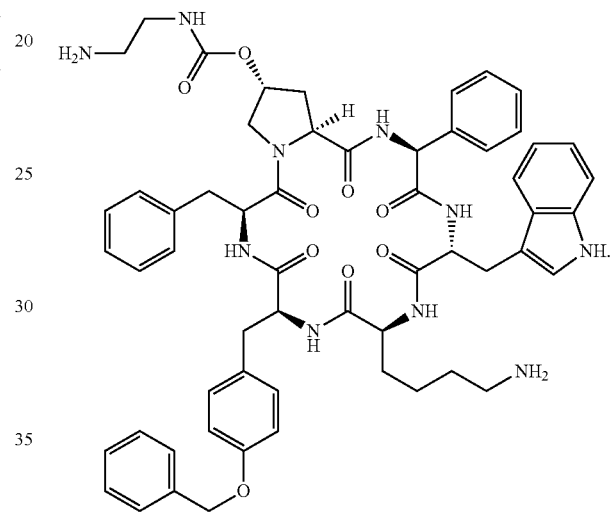

For the purposes of comparison, the structure of somatostatin-14 is as follows:

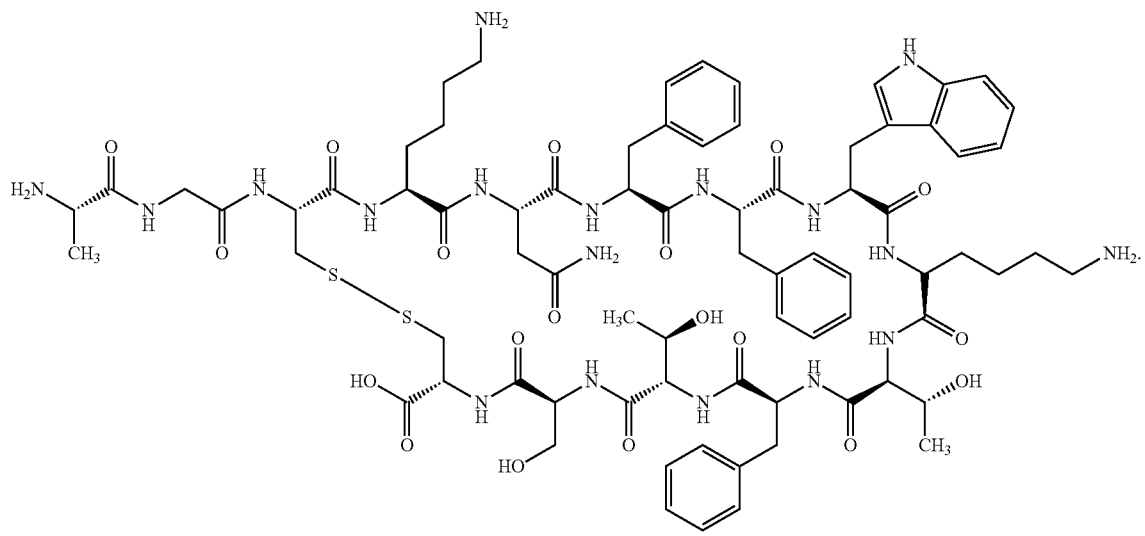

Thus, in a particular aspect, methods are provided for treatment of breast cancer, breast hyperplasia and/or prevention of breast cancer, including reduction in the progression of hyperplastic conditions to cancer, wherein increased frequency of PR/p63 double positive (PR/p63+) progenitor cells is detected, comprising administration of one or more somatostatin analogs which has affinity for SSTR3 and/or SSTR5 somatostatin receptors. The use of one or more somatostatin analog or other compound with enhanced affinity for SSTR3 and/or SSTR5 receptors, particularly versus SSTR1 and/or SSTR4 receptors in the treatment of breast or mammary hyperplasia and in the prevention or treatment of breast cancer in individuals at risk, wherein increased frequency of PR/p63+ progenitor cells is detected, is provided. The exemplary compound SOM230 has affinity for SSTR3 and/or SSTR5 receptors. BIM23A779 is described by Saveanu et al. (Neuroendocrinology, 2006, 83:258-263); Ben-Shlomo et al. (Molecular Endocrinology, 2007, Vol 21, No 10, pp 2565-2578); and Kidd et al. (Cancer, 2008, Vol 113, No 4, pp 690-700).

Somatostatin analogs and/or other compounds which bind or otherwise associate with and activate/signal the SSTR3 and/or SSTR5 receptors are suitable for use in the invention. The action of a somastostatin analog and its ability or capability to bind to or otherwise associate with SSTR3 and/or SSTR5 somatostatin receptor(s) can be determined by the skilled artisan or herein disclosed methods. Somatostatin analogs include but are not limited to BIM23A779 (Saveanu et al. Neuroendocrinology 83:258-263, 2006; Ben-Shlomo et al. Molecular Endocrinology, 2007, Vol 21, No 10, pp 2565-2578; Kidd et al. Cancer, 2008, Vol 113, No 4, pp 690-700, each of which is incorporated herein by reference in its entirety), AN-238 (Clin Cancer Research 7:2854-2861, 2001) (2-pyrrolinodoxorubicin (AN-201) linked to octapeptide carrier RC-121) (Nagy A et al (1998) Proc Natl Acad Sci USA 95:1794-1799), RC-121 (D-Phe-Cys-Tyr-D-Trp-Lys-Val-Cys-Thr-NH2) (Cai, R-Z et al (1986) Proc Natl Acad Sci USA 83:1896-1900), cyclic somatostatin analog peptide which selectively binds to the SRIF receptor SSTR3 (described in U.S. Pat. No. 6,579,967), and Somatostatin Tumor Inhibiting Analog (Anaspec). Nikiforovich has, moreover, used molecular modeling of constrained somatostatin analog peptides to probe SSTR specificity (Nikiforovich et al (2007) Chemical Biology and Drug Design 69(3):163-169). These studies serve as templates for design of conformationally-constrained non-peptide scaffolds that interact with specific SSTR subtypes.

The structure of AN-238, which includes RC-121, is as follows:

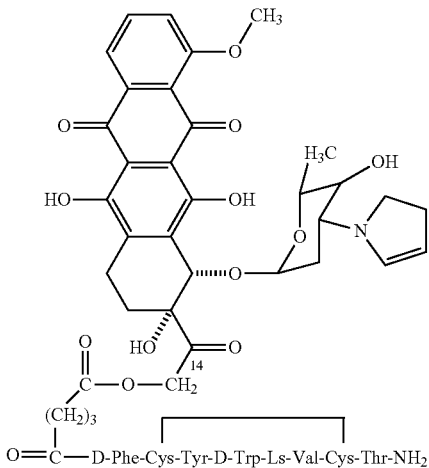

and the structure of RC-121 is as follows:

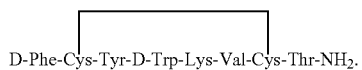

One skilled in the art can readily determine or assess the suitability of other compounds for use in the invention by, for example, screening in the LoxP model described herein to identify other compounds that reduce the number of PR/p63+ progenitor cells detected therein, or by determining its binding to and/or specificity for SSTR 3 and/or SSTR5 receptors, particularly in the breast.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Mutations can be made in the sequence of a somatostatin and/or somatostatin analog or compound of use in the invention such as to provide adequate amino acid. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)
Another grouping may be those amino acids with phenyl groups: Phenylalanine, Tryptophan, Tyrosine.

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to preferably reduce by at least about 30 percent, more preferably by at least 50 percent, most preferably by at least 90 percent, a clinically significant change in a pathological feature of a disease or condition. With respect to a tumor, a therapeutically effective amount could, for example, reduce the S phase activity of a target cellular mass, or other feature of pathology such as for example, elevated blood pressure, fever or white cell count as may attend its presence and activity.

The compounds, somatostatin or somatostatin analogs of use in the invention may be prepared in pharmaceutical compositions, with a suitable carrier and at a strength effective for administration by various means to a patient experiencing an adverse medical condition associated with a hyperplastic disorder and cystic disease of the breast, enhanced risk of breast cancer, and/or breast cancer, wherein increased frequency of PR/p63+ progenitor cells is detected, for the treatment thereof. A variety of administrative techniques may be utilized, among them parenteral techniques such as subcutaneous, intravenous and intraperitoneal injections, catheterizations and the like. Average quantities of the compounds, somatostatins, somatostatin analogs or their subunits may vary and in particular should be based upon the recommendations and prescription of a qualified physician or veterinarian.

Also, antibodies including both polyclonal and monoclonal antibodies, and drugs that modulate the production or activity of the somatostatins, and/or somatostatin receptors, particularly SSTR3 and/or SSTR5, may possess certain diagnostic applications and may for example, be utilized for the purpose of detecting and/or measuring conditions such as viral infection or the like. For example, the somatostatins, somatostatin analogs or their receptors may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the somatostatin analogs of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against somatostatins, and/or somatostatin receptor peptides can be screened for various properties; i.e., isotype, epitope, affinity, etc. Such monoclonals can be readily identified in activity assays. High affinity antibodies are also useful when immunoaffinity purification of native or recombinant somatostatins, somatostatin analogs or somatostatin receptors is possible or warranted.

Preferably, the anti-somatostatin or SSTR antibody used in the diagnostic methods of this invention is an affinity purified polyclonal antibody. More preferably, the antibody is a monoclonal antibody (mAb). In addition, it is preferable for the anti-somatostatin or SSTR antibody molecules used herein be in the form of Fab, Fab', F(ab')$_2$ or F(v) portions of whole antibody molecules.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal antibodies are also well-known in the art. See Niman et al., *Proc. Natl. Acad. Sci. USA,* 80:4949-4953 (1983). Typically, the somatostatin, somatostatin analogs or SSTR or a peptide analog is used either alone or conjugated to an immunogenic carrier, as the immunogen in the before described procedure for producing anti-somatostatin, somatostatin analogs or SSTR monoclonal antibodies. The hybridomas are screened for the ability to produce an antibody that immunoreacts with the somatostatin, somatostatin analogs or SSTR.

In contrast to expectations that mice comprising loxP sites flanking exon 11 of the BRCA1 gene (also referred to herein as LoxP mice) would develop normally, by 4 months of age they exhibited highly abnormal development including the formation of HANs, which are preneoplastic gland collections. Interestingly, when these animals were treated with SOM230, a significant effect on inhibiting abnormal ductal dilatation and preventing formation of HANs is observed.

As described herein, the present inventors have, moreover, discovered that LoxP mice harbor dramatically elevated levels of PR/p63+ progenitor cells. Detection of increased or elevated levels of PR/p63+ progenitor cells relative to wildtype levels can be used as a diagnostic and/or prognostic indicator in subjects at risk for developing a cancer or afflicted by cancer. Detection of increased or elevated levels of PR/p63+ progenitor cells relative to wildtype levels can be used, moreover, as a therapeutic indicator because detection of same in a cancer patient indicates that the cancer load (e.g., the number of progenitor cells) in the patient will be decreased by inhibitors of IGF-I activity. Determining the number of PR/p63+ progenitor cells in a patient undergoing treatment can also be used on an ongoing basis to evaluate efficacy of the treatment.

The present invention further contemplates therapeutic compositions useful in practicing the therapeutic methods of this invention. A subject therapeutic composition includes, in admixture, a pharmaceutically acceptable excipient (carrier) and one or more of a somatostatin, somatostatin analogs, polypeptide analog thereof or fragment thereof, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several milligrams of active ingredient per kilogram body weight of individual per day and depend on the route of administration. Suitable regimens for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

In a particular embodiment, the active ingredient is SOM230. In a more particular embodiment, SOM230 is administered to a human subject at a dose range of 200-1,200 micrograms (μg), twice daily (bid). In a more particular embodiment, SOM230 is administered to a human subject at 200, 300, 400, 500, 600, 700, 800, 900, 1,000 or 1,200 μg bid. In an even more particular embodiment, the SOM230 is administered subcutaneously (sc).

Also encompassed herein are embodiments of methods and uses thereof that call for pasireotide/SOM230 long acting release (pasireotide LAR), a long acting formulation of pasireotide. The chemical structures of pasireotide s.c. (A) and pasireotide LAR (B) are shown below for comparison:

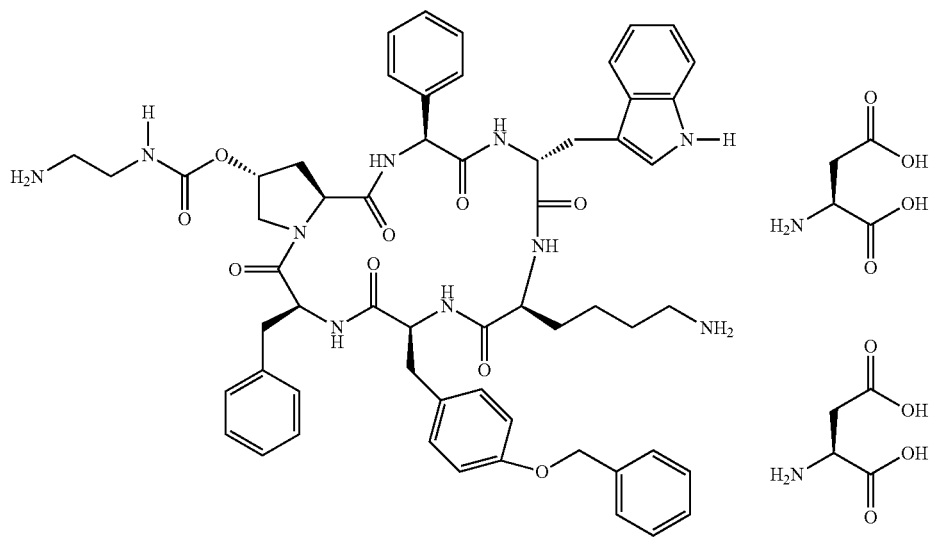

A

Pasireotide s.c.
Pasireotide diaspartate

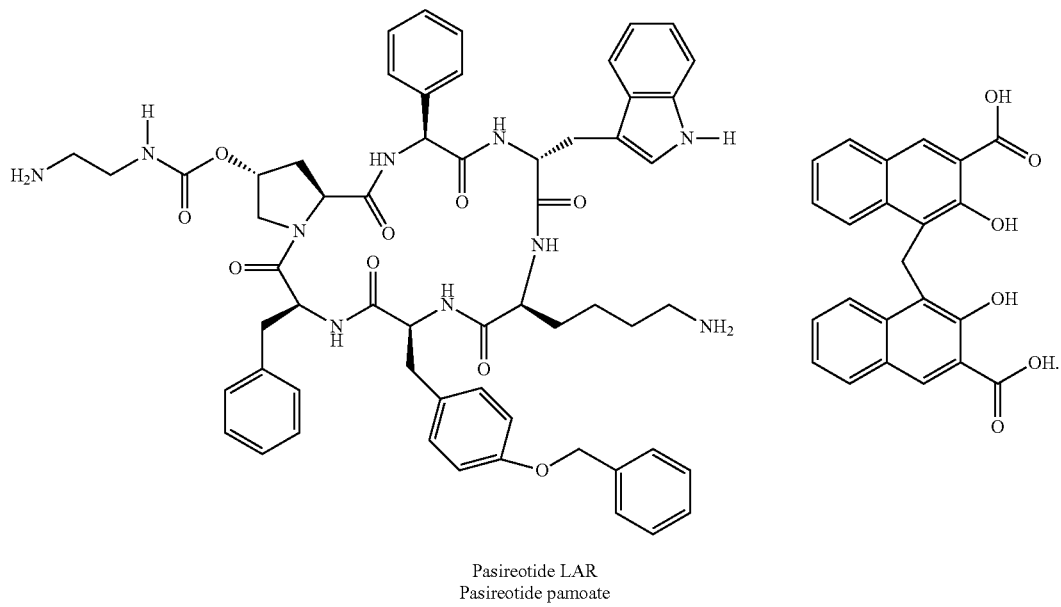

Pasireotide LAR
Pasireotide pamoate

See also Kvols et al. (Endocr Relat Cancer 2012 Jul. 17 [Epub ahead of print]; Chan et al. (Endocr Relat Cancer 2012 Jun. 26 [Epub ahead of print]; Dietrich et al. (Eur J Endocrinology 2012 May; 166(5):821-8. Epub 2012 Mar. 1); Oberg (Clin Oncol (R Coll Radiol) 2012 May; 24(4):282-93. doi: 10.1016/j.clon.2011.08.006. Epub 2011 Sep. 9; Colao (Abstract #OC1.1 2012 Joint 15$^{th}$ International Congress of Endocrinology and 14$^{th}$ European Congress of Endocrinology Meeting; May 5-9, 2012; Florence, Italy); and Oberg (Ann Oncol 2010 October; 21 Suppl 7:vii72-80); the entire content of each of which is incorporated herein by reference in its entirety.

In view of the undesirable side effects associated with SOM230 and somatostatin analogs in general, which include hyperglycemia, the present inventors propose herein alternative therapeutic regimens, wherein SOM230 is administered to human subjects in need thereof at 300-1,200 µg bid for 1-14 days. In a more particular embodiment, SOM230 is administered to a human subject at 600 µg bid for 1-14 days. More particularly, a 7-20 or a 7-10 day treatment duration is envisioned, followed by a rest period, wherein SOM230 is not administered. This is envisioned based on the inventors' understanding that the effect of SOM230 is more prolonged for decreasing the frequency of PR/p63+ progenitor cells than other endpoints due to the amount of time required for repopulation of this aberrant cell type. Irrespective of the particular therapeutic regimen selected, the objective is to reduce, for example, the number/frequency of PR/p63+ progenitor cells in the human subject and, thereafter, the human subject enters a rest period of 30-180 days or 20-60 days, wherein SOM230 is not administered. In a more particular embodiment, the rest period is established at 5 day intervals within the above ranges, for example, for 25, 30, 35, 40, 45, 50, 55, or 60 days. The above-described intermittent SOM230 therapeutic regimen is based on results presented herein which show that the beneficial effects of SOM230 are prolonged, even after discontinuing SOM230 administration. See, for example, FIGS. 3 and 4. Accordingly, an intermittent SOM230 dosing regimen such as that described herein will confer maximum therapeutic benefit to a subject, while minimizing adverse side effects experienced.

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method may be used to create analogs with unnatural amino acids.

The presence of SSTR3 and/or SSTR5 in cells can be ascertained by the usual immunological procedures applicable to such determinations. A number of useful procedures are known. Three such procedures which are especially useful utilize either the somatostatin, somatostatin analog or SSTR labeled with a detectable label, antibody $Ab_1$ labeled with a detectable label, or antibody $Ab_2$ labeled with a detectable label. The procedures may be summarized by the following equations wherein the asterisk indicates that the particle is labeled, and "~" stands for the somatostatin, somatostatin analog or SSTR:

$$\sim^* + Ab_1 = \sim^* Ab_1 \qquad \text{A.}$$

$$\sim + Ab^* = \sim Ab_1^* \qquad \text{B.}$$

$$\sim + Ab_1 + Ab_2^* = \sim Ab_1 Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody" or "DASP" procedure.

In each instance, the somatostatin, somatostatin analog or SSTR forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-somatostatin, somatostatin analog or SSTR antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

The present invention relates generally to the use and application of compounds or agents, including somatostatin analogs, with effect on, affinity for, or specificity to SSTR3 and/or SSTR5 somatostatin receptors, particularly in the breast, for the treatment of breast cancer, breast non-proliferative cystic disease and/or prevention or reduction of risk for breast cancer, wherein increased frequency of PR/p63+ progenitor cells is detected. The invention also relates to use of somatostatin analog SOM230 in treatment of same.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The somatostatin receptor(s) or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the somatostatin, somatostatin analog or SSTR may be radiolabeled and combined, for example, with antibodies or other inhibitors thereto, after which binding studies would be carried out. Solutions would then be prepared that contain various quantities of labeled and unlabeled uncombined somatostatin, somatostatin analog or SSTR, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn.

While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Methods and Materials

Simultaneous Immunofluorescence for PR and p63: 3-5 μm paraffin embedded tissue sections from C57/b and C57 loxP mice were stained using antibodies against PR and p63 (Lab Vision). Briefly, samples were deparaffinized by 60° C. heating following by xylene immersion for 30 min. Antigens were retrieved by heating 10 min 95° C. followed by 10 min 85° C. in citric acid pH 6.0 (Vector). To reduce non-specific background, samples were incubated for 1 h with casein 0.5% (Sigma). Samples were then incubated overnight at 4° C. with the corresponding primary antibodies to a final concentration of 1:20 and 1:200 for PR and p63 respectively. Next day, specific secondary goat anti mouse Alexa Fluor 488 and donkey anti rabbit Alexa Fluor 594 antibodies (Invitrogen) were used to a final concentration of 1:200 to detect the primary antibodies, by incubating the samples for 1 hour at room temperature. Finally, samples were counterstained using DAPI at 0.02 mg/ml and mounted with Vectashield (Vector). Samples were imaged using a 40× objective with 0.95 numerical aperture Zeiss Plan-Apochromat objective on a Zeiss Axiovert equipped with epifluorescence. The number of epithelial cells positive for PR, p63 or both, was then calculated as the relative frequency of positive cells per epithelial cells per image. Finally, frequencies of positive cells between animal groups were statistically analyzed with the chi-square distribution. A probability of $p<0.05$ was considered statistically significant.

Introduction

Women with BRCA1 mutations are at high risk for developing breast cancer. As described above, an animal model of Brca1 deficiency ($Brca1^{LoxP}/Brca1^{LoxP}$ mouse model system, also referred to herein as the LoxP mouse model system)

was developed in which the mammary glands are abnormally developed and which presents with a phenotype similar to that observed in women with BRCA1 mutations. The Brca1loxP/loxP phenotype is characterized by ductal dilatation and epithelial hyperplasia. In earlier studies, 4 month old Brca1loxP/loxP mice were treated with pasireotide, PQ401 (a small molecule kinase inhibitor of the IGF-I receptor), or vehicle for 7 days. At the end of that period, mammary development in drug- vs. vehicle-treated animals was compared. Results of these experiments demonstrated that medications that inhibit IGF-I action in the mammary gland prevent or reverse this phenotype, presumably due in part to reduced proliferation.

Results

The present inventors next sought to investigate further changes in cellular and molecular composition in Brca1$^{LoxP}$/Brca1$^{LoxP}$ mice and identify markers of breast cancer onset.

C57 loxP Mice Present an Increased Frequency of PR/p63 Double Positive Cells when Compared to C57/b Mice: The present inventors first analyzed the expression of both markers in the C57 loxP mice and compared that with the frequency of co-localizing cells observed in the C57/b (wildtype mice). A statistically significant difference (p<0.001) in the number of PR/p63 double positive cells was observed in the C57 loxP mice (22.5±0.8%) when compared to the C57 controls (3.8±0.4%). Thus, C57 loxP exhibit an increased frequency of PR/p63 co-localizing cells than the wild type control mice. See FIGS. 1A and 1B.

To investigate whether agents that inhibit IGF-I action in the mammary gland also inhibit cellular abnormalities associated with development of carcinoma, which include aberrant proliferation, differentiation/lineage commitment and genomic instability, the present inventors performed additional experiments to evaluate the effect of IGF-I inhibitors on the population of PR/p63 double positive progenitor cells in Brca1$^{LoxP}$/Brca1$^{LoxP}$ mice.

The Frequency of PR/p63 Double Positive Cells in C57 loxP is Significantly Reduced after Inhibition of IGFI with Pasireotide: The effect of treating the C57 loxP mice with pasireotide, an inhibitor of IGF-I activity, for 7 days was evaluated with respect to the frequency of PR/p63 double positive cells. The present inventors found a statistically significant decrease (p<0.001) in the frequency of PR/p63 double positive cells in the treated animals (4.8±1.2%), as compared to that of the C57 loxP untreated mice (22.5±0.8%). Interestingly, the frequency of PR/p63 double positive cells in the treated mice was reduced to be equivalent to the control C57/b mice. See FIG. 1B.

These results demonstrate that both SOM230 (pasireotide) and PQ401 significantly reduce the number of aberrant cells in the mammary glands of Brca1 deficient (C57 loxP; Brca1$^{LoxP}$/Brca1$^{LoxP}$) mice. In light of these results, the present inventors have identified novel in situ markers of aberrant lineage commitment and shown that this specific population (i.e., PR/p63 double positive cells) can be significantly inhibited by blocking IGF-I action by two different agents (pasireotide and PQ401).

As shown in FIG. 2, treatment with inhibitors of IGF-I activity dramatically reduces the level of genomic instability observed. Indeed, the number of cells exhibiting genomic instability is essentially reduced to that observed in wildtype animals. FIG. 2A shows immunolocalization of γ-tubulin (green), which is used to locate centrosomes in the mammary glands of wildtype (WT) or Brca1 deficient (Brca1$^{LoxP}$/Brca1$^{LoxP}$) mice. Nuclei (blue) are counterstained. In wildtype mice, 1 or 2 centrosomes per cell are observed, reflecting normal, control numbers of centrosomes in individual cells. In contrast, LoxP mice comprise a population of cells that have significantly more than 1 or 2 centrosomes per cell (white arrow indicates an exemplary cell in this population). FIG. 2B shows a graph depicting quantitation of the centrosome index (normal equals 1) for wildtype (normal control) and LoxP mice, which analysis reveals that the frequency of these cells is significantly reduced by 7 days pretreatment with PQ401 or SOM230, both of which inhibit IGF-1 activity.

This is the first demonstration that IGF-I inhibition can inhibit aberrant lineages and genomic instability, both of which are associated with increased risk of developing breast cancer, including basal breast cancer. Thus, IGF-I inhibition not only prevents cell proliferation, but specifically deletes the most susceptible cell population. This conclusion is based on the observation that the number of cells is rapidly reduced by IGF-I inhibition, concomitant with this population. Deletion is the most likely mechanism due to the short duration of treatment (7 days) and the specific decrease in the frequency of these cells. Experiments are underway to determine if apoptosis is the specific deletion mechanism. This combination of markers thus provides a unique prognostic feature that can be used to screen agents that can prevent breast cancer in mouse models or high risk women. Previously, breast cancer risk has been based on certain genetic predispositions, which cannot be altered or prevented. Data presented herein using the Brca1$^{LoxP}$/Brca1$^{LoxP}$ mouse model suggest that a specific set of markers (PR and p63) can be used, in combination, to evaluate the efficacy of risk reduction therapies, as well as used to stratify patients who will benefit from specific preventive therapies. While occurring in the context of Brca1 deficiency, it is reasonable to speculate that such changes also occur spontaneously in breast and in other tissues.

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

Various references are cited throughout this Specification, each of which is incorporated herein by reference in its entirety.

What is claimed is:

1. A method for treating breast cancer in a mammal, the method comprising administering at least one inhibitor of insulin-like growth factor I (IGF-I) activity to the mammal, wherein the at least one inhibitor is SOM230 or pasireotide/SOM230 long acting release (pasireotide LAR) and is administered in accordance with an intermittent dosing regimen whereby treatment periods are interrupted by rest periods wherein the at least one inhibitor of IGF-I activity is not administered to the mammal, and the rest periods permit recovery from side effects due to administration of the at least one inhibitor of IGF-I activity.

2. The method of claim 1, wherein an elevated frequency of PR/p63+ progenitor cells is detected in the mammal.

3. The method of claim 1, wherein the mammal is a BRCA1 mutation carrier.

4. The method of claim 1, wherein the elevated frequency of PR/p63+progenitor cells is at least 2 times or at least 4 times that determined in a wildtype mammal.

5. The method of claim 1, wherein the number of PR/p63+ progenitor cells is determined in a tissue sample isolated from the mammal.

6. The method of claim 1, wherein the mammal is a human.

7. The method of claim 1, wherein the treatment periods range from 7-20 days.

8. The method of claim 1, wherein the rest periods range from 30-180 days.

9. The method of claim 1, further comprising repetitive cycles of the intermittent dosing regimen.

* * * * *

UNITED STATES PATENT AND TRADEMARK OFFICE
CERTIFICATE OF CORRECTION

PATENT NO. : 9,408,887 B2
APPLICATION NO. : 14/487197
DATED : August 9, 2016
INVENTOR(S) : D. Kleinberg et al.

Page 1 of 1

It is certified that error appears in the above-identified patent and that said Letters Patent is hereby corrected as shown below:

In the Specification

At Column 1, Line 16, at "Governmental Support", replace:
"The research leading to the present invention was supported, at least in part, by a grant from the Office of Biological and Environmental Research DE-FG01-08ER64654. Accordingly, the Government has certain rights in the invention."

With:
--This invention was made with government support under Grant No. W81XWH-11-1-0779 awarded by the Office of Biological and Environmental Research. The Government has certain rights in this invention.--

Signed and Sealed this
Twenty-third Day of April, 2019

Andrei Iancu
*Director of the United States Patent and Trademark Office*

UNITED STATES PATENT AND TRADEMARK OFFICE
CERTIFICATE OF CORRECTION

PATENT NO. : 9,408,887 B2
APPLICATION NO. : 14/487197
DATED : August 9, 2016
INVENTOR(S) : David L. Kleinberg et al.

It is certified that error appears in the above-identified patent and that said Letters Patent is hereby corrected as shown below:

In the Specification

At Column 1, Lines 16-20, after GOVERNMENTAL SUPPORT, replace:
"This invention was made with government support under Grant No. W81XWH-11-1-0779 awarded by the Office of Biological and Environmental Research. The Government has certain rights in this invention."

With:
--This invention was made with government support under grant numbers W81XWH-11-1-0779 and W81XWH-11-1-0780 awarded by the Department of Defense. The government has certain rights in the invention.--

This certificate supersedes the Certificate of Correction issued April 23, 2019.

Signed and Sealed this
Twenty-fourth Day of January, 2023

Katherine Kelly Vidal
*Director of the United States Patent and Trademark Office*